(12) United States Patent
de Palo et al.

(10) Patent No.: US 10,596,276 B2
(45) Date of Patent: *Mar. 24, 2020

(54) STABLE, CONCENTRATED RADIONUCLIDE COMPLEX SOLUTIONS

(71) Applicant: Advanced Accelerator Applications (Italy) Srl, Pozzilli (IT)

(72) Inventors: Francesco de Palo, Ivrea (IT); Lorenza Fugazza, Ivrea (IT); Donato Barbato, Ivrea (IT); Maurizio Mariani, Ivrea (IT); Daniela Chicco, Albiano d'Ivrea (IT); Giovanni Tesoriere, Noicattaro (IT); Clementina Brambati, Turin (IT)

(73) Assignee: ADVANCED ACCELERATOR APPLICATIONS (ITALY) S.R.L., Pozzilli (Isernia) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/175,261

(22) Filed: Oct. 30, 2018

(65) Prior Publication Data

US 2020/0030464 A1 Jan. 30, 2020

Related U.S. Application Data

(63) Continuation-in-part of application No. 16/140,962, filed on Sep. 25, 2018, which is a continuation-in-part of application No. 16/045,484, filed on Jul. 25, 2018.

(51) Int. Cl.
| | |
|---|---|
| *A61K 51/00* | (2006.01) |
| *A61M 36/14* | (2006.01) |
| *A61K 51/04* | (2006.01) |
| *C22B 59/00* | (2006.01) |
| *A61K 33/24* | (2019.01) |

(52) U.S. Cl.
CPC ............ *A61K 51/048* (2013.01); *A61K 33/24* (2013.01); *C22B 59/00* (2013.01); *A61K 51/0482* (2013.01)

(58) Field of Classification Search
None
See application file for complete search history.

(56) References Cited

U.S. PATENT DOCUMENTS

| | | | |
|---|---|---|---|
| 5,753,627 A | 5/1998 | Albert et al. | |
| 5,776,894 A | 7/1998 | Albert et al. | |
| 5,804,157 A | 9/1998 | Srinivasan et al. | |
| 5,830,431 A | 11/1998 | Srinivasan et al. | |
| 6,123,916 A | 9/2000 | Krenning et al. | |
| 6,183,721 B1 | 2/2001 | Albert et al. | |
| 6,277,356 B1 | 8/2001 | Albert et al. | |
| 2007/0269375 A1* | 11/2007 | Chen | A61K 51/088 424/1.69 |

FOREIGN PATENT DOCUMENTS

| | | |
|---|---|---|
| EP | 0515313 B1 | 8/2000 |
| WO | 199701579 A2 | 1/1997 |
| WO | 200210192 A2 | 2/2002 |
| WO | 2008009444 A1 | 1/2008 |
| WO | 2013167130 A1 | 11/2013 |
| WO | 2015063746 A1 | 5/2015 |
| WO | 2015171792 A1 | 11/2015 |
| WO | 2016207732 A1 | 12/2016 |
| WO | 2018074918 A1 | 4/2018 |
| WO | 2018081860 A1 | 5/2018 |

OTHER PUBLICATIONS

De Blois et al. (Appl. Radiat. Isotop. 2014, 85, 28-33).*
Of Singh et al. (Ind. J. Nucl. Med. 2011, 26, 135-138).*
RCM meeting (Development and preclinical evaluation of therapeutic radiopharmaceuticals based on 177Lu- and 90Y-labelled monoclonal antibodies and peptides: Stip, Republic of Macedonia Oct. 1-5, 2012).*
Breeman et al., Optimising Conditions for Radiolabelling of DOTA-peptides with 90Y, 111In and 177Lu at High Specific Activities, Eur J Nucl Med Mol Imaging, (2003), 30, 917-920.
Breeman et al., Overview of Development and Formulation of 177Lu-DOTA-TATE for PRRT, Current Radiopharmaceuticals, (2016), 9, 8-18.
Maus et al., Aspects on radiolabeling of 177Lu-DOTA-TATE: After C18 purification re-addition of ascorbic acid is required to maintain radiochemical purity, Int J. Diagnostic Imaging, (2014), 1, 5-12.
Liu et al., Ascorbic Acid: Useful as a Buffer Agent and Radiolytic Stabilizer for Metalloradiopharmaceuticals, Bioconjugate Chem, (2003), 14, 1052-1056.
Liu et al., Stabilization of 90Y-Labeled DOTA-Biomolecule Conjugates Using Gentisic Acid and Ascorbic Acid, Bioconjugate Chem, (2001), 12, 554-558.
Banerjee et al., Lutetium-177 Therapeutic Radiopharmaceuticals: Linking Chemistry, Radiochemistry, and Practical Applications, Chem Rev, (2015), 115, 2934-2974.
Declaration for Grace Period filed in PCT/IB2018/057415, Sep. 25, 2018.
Declaration for Grace Period filed in PCT/IB2018/055575, Jul. 25, 2018.
Aslani et al., Lutetium-177 DOTATATE Production with and Automated Radio-pharmaceutical Synthesis System, Asia Oceania Journal of Nuclear Medicine & Biology, (2015), 3, 107-115.

(Continued)

*Primary Examiner* — Michael G. Hartley
*Assistant Examiner* — Melissa J Perreira
(74) *Attorney, Agent, or Firm* — Lian Ouyang

(57) ABSTRACT

The present invention relates to radionuclide complex solutions of high concentration and of high chemical stability, that allows their use as drug product for diagnostic and/or therapeutic purposes. The stability of the drug product is achieved by at least one stabilizer against radiolytic degradation. The use of two stabilizers introduced during the manufacturing process at different stages was found to be of particular advantage.

24 Claims, No Drawings

(56) References Cited

OTHER PUBLICATIONS

Lutathera, Advanced Accelerator Applications, Highlights of Prescribing Information, Jan. 2018.
Lutathera, European Medicines Agency, EPAR Public Assessment Report, First Published Jan. 17, 2018.
Lutathera, European Medicines Agency, EPAR Product Information, First Published Jan. 17, 2018, last updated Apr. 11, 2018.
Lutathera, European Medicines Agency, CHMP Summary Positive Opinion, First Published Jul. 21, 2017.
Luna-Gutierrez et al., Freeze-Dried multi-dose kits for the fast preparation of 177Lu-Tyr3-octreotide and 177Lu-PSMA(inhibitor) under GMP conditions, J Radioanal Nucl Chem, (2017), 314, 2181-2188.
Das et al., Preparation of DOTA-TATE and DOTA-NOC freeze-dried kits for formulation of patient doses of 177Lu-labeled agents and their comparison for peptide receptor radionuclide therapy application, J Radioanal Nucl Chem, (2014) 299, 1389-1398.
De Blois et al., Effectiveness of Quenchers to Reduce Radiolysis of 111In-or 177-Lu-Labelled Methionine-Containing Regulatory Peptides. Maintaining Radiochemical Purity as Measured by HPLC, Current Topics in Med Chem, (2012), 12, 2677-2685.
Wild et al., DOTA-NOC, a high-affinity ligand of somatostatin receptor subtypes 2, 3 and 5 for labelling with various radiometals, Eur J Nucl Med Mol Imaging, (2003), 30, 1338-1347.
Kwekkeboom et al., [177-Lu-DOTA0, Tyr3]octreotate: comparison with [111In-DTPA0]octreotide in patients, Eur J Nucl Med Mol Imaging, (2001), 28, 1319-1325.
Das et al., Preparation of Therapeutic Dose of 177Lu-DOTA-TATE Using a Novel Single Vial Freeze-dried Kit: A Comparison with 'In-situ' Preparation at Hospital Radiopharmacy, Current Radiopharmaceuticals, (2014) 7, 12-19.
Mathur et al., Bulk Scale Formulation of Therapeutic Dosed of Clinical Grade Ready-to-Use 177Lu-DOTA-TATE: The Intricate Radiochemistry Aspects, Cancer Biotherapy and Radiopharmaceuticals, (2017), 32, 7, 266-273.
Advanced Accelerator Applications Announces European Approval of Lutetium (177Lu) Oxodotreotide (Lutathera®) for Gastroenteropancreatic Neuroendocrine (GEP-NET) Tumors, Press Release Sep. 29, 2017.
Advanced Accelerator Applications Receives US FDA Approval for Lutathera® for Treatment of Gastroenteropancreatic Neuroendocrine Tumors, Press Release Jan. 26, 2018.
Frilling et al., "Treatment with 90Y- and 177Lu-DOTATOC in patients with metastatic neuroendocrine tumors", Surgery, vol. 140, pp. 968-977, 2006.

* cited by examiner

STABLE, CONCENTRATED RADIONUCLIDE COMPLEX SOLUTIONS

RELATED APPLICATIONS

This application is a continuation-in-part application of U.S. application Ser. No. 16/140,962 filed Sep. 25, 2018, which is a continuation-in-part of U.S. application Ser. No. 16/045,484 filed Jul. 25, 2018 and claims priority to, and the benefit of International Application No. PCT/IB2018/055575 filed Jul. 25, 2018, the contents of each of which are hereby incorporated by reference in their entireties.

FIELD OF THE INVENTION

The present invention relates to radionuclide complex solutions of high concentration and of high chemical and radiochemical stability, that allows their use as commercial drug product for diagnostic and/or therapeutic purposes.

BACKGROUND OF THE INVENTION

The concept of targeted drug delivery is based on cell receptors which are overexpressed in the target cell in contrast to the not-to-be-targeted cells. If a drug has a binding site to those overexpressed cell receptors it allows the delivery of the drug after its systemic administration in high concentration to those target cells while leaving other cells, which are not of interested, unaffected. For example, if tumor cells are characterized by an overexpression of a specific cell receptor, a drug with binding affinity to said receptor will after intravenous infusion accumulate in high concentration in the tumor tissue while leaving the normal tissue unaffected.

This targeted drug delivery concept has also been used in radiomedicine to deliver radionuclides selectively to the target cells for diagnostic or therapeutic purposes.

For this radiomedicinal application the target cell receptor binding moiety is typically linked to a chelating agent which is able to form a strong complex with the metal ions of a radionuclide. This radiopharmaceutical drug is then delivered to the target cell and the decay of the radionuclide is then releasing high energy electrons, positrons or alpha particles as well as gamma rays at the target site.

One technical problem with those radiopharmaceutical drug products is that the decay of the radionuclide occurs constantly, e.g. also during the manufacturing and during storage of the drug product, and the released high energy emissions induce the cleavage of the chemical bonds of the molecules which form part of the drug product. This is often referred to as radiolysis or radiolytic degradation. The radiolytic degradation of the receptor binding moiety of the drug may lead to a decrease in its efficacy to act as a diagnostic and/or therapeutic.

The poor stability of those radiopharmaceutical drug products and their lack of any significant shelf-life required that those drugs have so far to be manufactured as an individual patient's dose unit in the laboratories at the hospital and administered immediately to the patient who had to be present at that hospital already awaiting the radiological treatment. To facilitate such drug preparation in the hospital laboratories, "cold" (i.e. non-radioactive) freeze-dried kits have been developed which comprise the cell receptor binding moiety linked to a chelating agent without the radionuclide. The freeze-dried content of those kit vials is then to be reconstituted with a solution of the radionuclide short before administration (Das et al. *J Radioanal Nucl Chem* 2014, 299, 1389-1398; Das et al. *Current Radiopharmaceuticals* 2014, 7, 12-19; Luna-Gutierrez et al. *J Radioanal Nucl Chem* 2017, 314, 2181-2188). However, those kits are not "ready-to-use" as they require the reconstitution step and in addition further processing steps (e.g. applying heat for the complexation reaction) as well as purification and sterilization steps before the drug can be finally administered.

To reduce radiolysis of radiopharmaceutical drug products and thus improve stability, various strategies have been explored with more or less success: The drug product may be stored at low temperatures, or produced in high dilution, or stabilizers may be added.

Adding stabilizers however may be problematic as those chemicals may have a negative impact on the complexation of the radionuclide into the chelating agent or may have a limited solubility and precipitate from the solution. Ethanol has been reported as stabilizer against radiolysis (WO 2008/009444). While ethanol might not have a negative impact on the complexation or a solubility issue, higher amounts of ethanol in an infusion solution may be physiologically problematic and may have a negative impact on the tolerability of the drug product.

Producing the drug product in high dilution has the disadvantage that large volumes of infusion solutions need to be administered to patients. For the convenience of patients and for drug tolerability reasons it would be highly desirable to provide the radiopharmaceutical drug product in a high concentration. Those highly concentrated solutions however are in particular prone to radiolysis. Therefore, there are contradictory positions between, on the one hand, avoiding radiolysis by dilution of the drug product but, on the other hand, avoiding patient discomfort during treatment by providing a concentrated drug solution. In Mathur et al. *Cancer Biotherapy and Radiopharmaceuticals*, 2017, 32(7), 266-273 a product of high concentration has been reported and claimed being ready-to-use. However, that composition may be problematic with respect to tolerability as it contains high amounts of ethanol.

It remains therefore a challenge to design a ready-to-use radiopharmaceutical drug product which can be produced at commercial scale and delivered as a sufficiently stable and sterile solution in a high concentration which leads to a convenient small infusion volume for patients and which has a composition of high physiological tolerability (e.g. a composition which does not contain ethanol).

SUMMARY OF THE INVENTION

The present inventors have now found a way to design and produce a highly concentrated radionuclide complex solution which is chemically and radiochemically very stable even if stored at ambient or short term elevated temperatures so that it can be produced on commercial scale and supplied as ready-to-use radiopharmaceutical product.

The present invention is provided in various aspects as outlined in the following:
  A pharmaceutical aqueous solution comprising
    (a) a complex formed by
      (ai) a radionuclide, and
      (aii) a cell receptor binding organic moiety linked to a chelating agent; and
    (b) at least one stabilizer against radiolytic degradation;
  wherein
  said radionuclide is present in a concentration that it provides a volumetric radioactivity of at least 100 MBq/mL, preferably of at least 250 MBq/mL.

Said stabilizer(s), component (b), is (are) present in a total concentration of at least 0.2 mg/mL, preferably at least 0.5 mg/mL, more preferably at least 1.0 mg/mL, even more preferably at least 2.7 mg/mL.

A pharmaceutical aqueous solution, comprising
(a) a complex formed by
  (ai) the radionuclide $^{177}$Lutetium (Lu-177), present in a concentration that it provides a volumetric radioactivity of from 250 to 500 MBq/mL, and
  (aii) the chelating agent linked somatostatin receptor binding organic moiety DOTA-TATE (oxodotreotide) or DOTA-TOC (edotreotide);
(bi) gentisic acid or a salt thereof as the first stabilizer against radiolytic degradation present in a concentration of from 0.5 to 1 mg/mL;
(bii) ascorbic acid or a salt thereof as the second stabilizer against radiolytic degradation present in a concentration of from 2.0 to 5.0 mg/mL.

A process for manufacturing said pharmaceutical aqueous solution as defined above, comprising the process steps:
(1) Forming a complex of the radionuclide and the chelating agent linked cell receptor binding organic moiety by
  (1.1) preparing an aqueous solution comprising the radionuclide;
  (1.2) preparing an aqueous solution comprising the chelating agent linked cell receptor binding organic moiety, a first stabilizer, optionally a second stabilizer; and
  (1.3) mixing the solutions obtained in steps (1.1) and (1.2) and heating the resulting mixture;
(2) Diluting the complex solution obtained by step (1) by
  (2.1) preparing an aqueous dilution solution optionally comprising a second stabilizer; and
  (2.2.) mixing the complex solution obtained by step (1) with the dilution solution obtained by the step (2.1).

The present invention provide the following advantages:

The high concentration allows administering a high dose within a short time frame. E.g. in the case of $^{177}$Lu-DOTA-TATE, the high dose of 7.4 GBq can be provided in a small volume of 20.5 to 25.0 mL which allows the IV infusion administration to be completed within about 20 to 30 minutes.

The use of suitable stabilizer(s), according to the present invention as described, herein ensures high stability, at least 95%, 96%, 97%, 98%, 99% or 100% chemical stability with respect to the chemical purity for the cell receptor-binding molecule after 72 hours at 25° C., even if this molecule is a sensitive peptide molecule. E.g. for DOTA-TATE 100% chemical purity were found after 72 hours at 25° C. and even after 48 hours at 32° C. were found. Even under short term elevated temperature conditions (32° C. for 12 h and 25° for 60 h) such high stability was found with respect to chemical purity.

Further, the use of suitable stabilizer(s), according to the present invention as described, herein ensures high stability, at least 95% radiochemical stability with respect to the radiochemical purity radionuclide complex. E.g. for $^{177}$Lu-DOTA-TATE at least 95% radiochemical purity were found after 72 hours at 25° C. Even under short term elevated temperature conditions (32° C. for 12 h and 25° for 60 h) such high stability was found with respect to radiochemical purity.

While sufficient stability may be achieved already with one single stabilizer, the use of two stabilizers has been found to be of particular suitability in stabilizing sensitive radiopharmaceutical solutions. In particular, the presence of one stabilizer during complex formation and another stabilizer added after the complex formation is of advantage as it ensures that already during the complexation reaction, the cell receptor-binding molecule is protected against radiolysis and the other stabilizer enhances the protecting effect for the shelf-life period. Further, by this sequential application of the two stabilizers it is ensured, that during complexation only a relatively small amount of stabilizer is present (which minimizes the potential interference of that stabilizer with the complexation reaction) and after complexation a large amount of a stabilizer combination is present (which strengthens the protective power of the stabilizers for the following drug product storage time period).

This sequential application of two stabilizers also reduces the overall thermal stress of those stabilizers as one of them is not present when the complexation reaction, which involves high temperatures, takes place.

Further, particularly the use of two different stabilizers is advantageous as this combination is more efficacious in reacting to the various different radicals possibly formed by the radiolysis of the cell receptor binding molecule than only one single stabilizer can do.

The composition of the radiopharmaceutical solution does not require the presence of ethanol. The solution is sufficiently stable without ethanol. The absence of ethanol is of advantage with respect to the physiological tolerability of the solution.

A shelf-life of at least 3 days is required to allow a radiopharmaceutical drug product to be manufactured from a centralized pharmaceutical production site and to commercialize it as a ready-to-use drug product.

Therefore, due to the high stability (72 h at 25° C.) the present invention allows centralized pharmaceutical production at highest quality standards (e.g. cGMP) and at industrial scale, e.g. at 74 GBq or 148 GBq batch size which provides the drug product in numerous dose units, e.g. enough dose units for the treatment of 10 to 20 patients at the same time.

Further, due to the high stability, there is sufficient time for the present invention to be shipped from a centralized pharmaceutical production site to remote clinical centers.

Even further, due to the high stability, the present invention can be provided as a ready-to-use infusion solution which can be immediately administered to the patient without a need for the clinical staff to perform any preparatory work before administration.

The present invention of particular suitability for the somatotatin receptor binding peptides, here in particular for the very sensitive somatostatin analogues octreotide and octreotate which are in particular prone to degradation reactions. Further, the present invention of particular suitability for the radionuclide Lutetium-177 with its specific radioactivity characteristics.

DETAILED DESCRIPTION OF THE INVENTION

Herein after, the present invention is described in further detail and is exemplified.

In general, the present invention is concerned about a pharmaceutical aqueous solution, in particular a radiopharmaceutical aqueous solution. The solution is for intravenous (IV) use/application/administration. The solution is stable, concentrated, and ready-to-use.

The stability of the solution ascertained by the use of stabilizers against radiolytic degradation.

In general, the stabilizers used in accordance with the present inventions may be selected from gentisic acid (2,5-dihydroxybenzoic acid) or salts thereof, ascorbic acid (L-ascorbic acid, vitamin C) or salts thereof (e.g. sodium ascorbate), methionine, histidine, melatonin, ethanol, and Se-methionine. Preferred stabilizers are selected from gentisic acid or salts thereof and ascorbic acid or salts thereof.

Ethanol is considered as less preferred stabilizer due to tolerability issues associated with it if present in higher concentrations. Ethanol should be ideally avoided in the solutions of the present invention (in other words: free of ethanol), at least the amount of ethanol in the solutions of the present invention should be limited, e.g. less than 5%, preferably less than 2%, more preferably less than 1% in the final solution which is foreseen to be injected/infused. Even more preferably, the solution is free of ethanol.

In accordance with the present invention the following embodiments are provided:

1. A pharmaceutical aqueous solution comprising
   (a) a complex formed by
      (ai) a radionuclide, and
      (aii) a cell receptor binding organic moiety linked to a chelating agent; and
   (b) at least one stabilizer against radiolytic degradation; wherein
   said radionuclide is present in a concentration that it provides a volumetric radioactivity of at least 100 MBq/mL, preferably of at least 250 MBq/mL.
2. The pharmaceutical aqueous solution according to embodiment 1,
   wherein said stabilizer(s), component (b), is (are) present in a total concentration of at least 0.2 mg/mL, preferably at least 0.5 mg/mL, more preferably at least 1.0 mg/mL, even more preferably at least 2.7 mg/mL.
3. The pharmaceutical aqueous solution according to any one of the preceding embodiments, wherein said radionuclide is present in a concentration that it provides a volumetric radioactivity of from 100 to 1000 MBq/mL, preferably from 250 to 500 MBq/mL.
4. The pharmaceutical aqueous solution according to any one of the preceding embodiments, wherein said stabilizer(s) is (are) present in a total concentration of from 0.2 to 20.0 mg/mL, preferably from 0.5 to 10.0 mg/mL, more preferably from 1.0 to 5.0 mg/mL, even more preferably from 2.7 to 4.1 mg/mL.
5. The pharmaceutical aqueous solution according to any one of the preceding embodiments,
   wherein the component (b) is only one stabilizers against radiolytic degradation, i.e. only a first stabilizer.
6. The pharmaceutical aqueous solution according to any one of the preceding embodiments,
   wherein the component (b) are at least two stabilizers against radiolytic degradation, i.e. at least a first and a second stabilizer, preferably only two stabilizers, i.e. only a first and a second stabilizer.
7. The pharmaceutical aqueous solution according to any one of the embodiments 5 to 6, wherein the first stabilizer is present in a concentration of from 0.2 to 5 mg/mL, preferably from 0.5 to 5 mg/mL, more preferably from 0.5 to 2 mg/mL, even more preferably from 0.5 to 1 mg/mL, even more preferably from 0.5 to 0.7 mg/mL.
8. The pharmaceutical aqueous solution according to embodiment 6 or 7, wherein the second stabilizer is present in a concentration of from 0.5 to 10 mg/mL, more preferably from 1.0 to 8.0 mg/mL, even more preferably from 2.0 to 5.0 mg/mL, even more preferably from 2.2 to 3.4 mg/mL.
9. The pharmaceutical aqueous solution according to any one of the preceding embodiments, wherein the stabilizer(s) is (are) selected from gentisic acid (2,5-dihydroxybenzoic acid) or salts thereof, ascorbic acid (L-ascorbic acid, vitamin C) or salts thereof (e.g. sodium ascorbate), methionine, histidine, melatonin, ethanol, and Se-methionine, preferably selected from gentisic acid or salts thereof and ascorbic acid or salts thereof.
10. The pharmaceutical aqueous solution according to any one of the embodiments 5 to 9, wherein the first stabilizer is selected from gentisic acid and ascorbic acid, preferably the first stabilizer is gentisic acid.
11. The pharmaceutical aqueous solution according to any one of the embodiments 6 to 10, wherein the second stabilizer is selected from gentisic acid and ascorbic acid, preferably the second stabilizer is ascorbic acid.
12. The pharmaceutical aqueous solution according to any one of the embodiments 6 to 8, wherein the first stabilizer is gentisic acid or a salt thereof and the second stabilizer is ascorbic acid or a salt thereof, and the ratio of the concentration (in mg/mL) of the first stabilizer to the concentration (in mg/mL) of the second stabilizer is from 1:3 to 1:7, preferably from 1:4 to 1:5.
13. The pharmaceutical aqueous solution according to any one of the preceding embodiments, wherein the radionuclide is selected from $^{177}$Lu, $^{68}$Ga, $^{18}$F, $^{99m}$Tc, $^{211}$At, $^{82}$Rb, $^{166}$Ho, $^{225}$Ac, $^{111}$In, $^{123}$I, $^{131}$I, $^{89}$Zr, $^{90}$Y, preferably selected from $^{177}$Lu and $^{68}$Ga, more preferably is $^{177}$Lu.
14. The pharmaceutical aqueous solution according to any one of the preceding embodiments, wherein the cell receptor binding moiety is a somatostatin receptor binding peptide, preferably said somatostatin receptor binding peptide is selected from octreotide, octreotate, lanreotide, vapreotide and pasireotide, preferably selected from octreotide and octreotate.
15. The pharmaceutical aqueous solution according to any one of the preceding embodiments, wherein the chelating agent is selected from DOTA, DTPA, NTA, EDTA, DO3A, NOC and NOTA, preferably is DOTA.
16. The pharmaceutical aqueous solution according to any one of the preceding embodiments, wherein the cell receptor binding moiety and the chelating agent form together molecules selected from DOTA-OC, DOTA-TOC (edotreotide), DOTA-NOC, DOTA-TATE (oxodotreotide), DOTA-LAN, and DOTA-VAP, preferably selected from DOTA-TOC and DOTA-TATE, more preferably is DOTA-TATE.
17. The pharmaceutical aqueous solution according to any one of the preceding embodiments, wherein the radionuclide, the cell receptor binding moiety and the chelating agent form together the complex $^{177}$Lu-DOTA-TOC ($^{177}$Lu-edotreotide) or $^{177}$Lu-DOTA-TATE ($^{177}$Lu-oxodotreotide), preferably $^{177}$Lu-DOTA-TATE.
18. The pharmaceutical aqueous solution according to any one of the preceding embodiments, further comprising a buffer, preferably said buffer is an acetate buffer, preferably in an amount to result in a concentration of from 0.3 to 0.7 mg/mL (preferably about 0.48 mg/mL) acetic acid and from 0.4 to 0.9 mg/mL (preferably about 0.66 mg/mL) sodium acetate.
19. The pharmaceutical aqueous solution according to any one of the preceding embodiments, further comprising a sequestering agent, preferably said sequestering agent is diethylentriaminepentaacetic acid (DTPA) or a salt thereof, preferably in an amount to result in a concentration of from 0.01 to 0.10 mg/mL (preferably about 0.05 mg/mL).

20. The pharmaceutical aqueous solution according to any one of the preceding embodiments, which has a shelf life of at least 24 hours (h) at ≤25° C., at least 48 h at ≤25° C., at least 72 h at ≤25° C., of from 24 h to 120 h at ≤25° C., from 24 h to 96 h at ≤25° C., from 24 h to 84 h at ≤25° C., from 24 h to 72 h at ≤25° C., in particular has a shelf life of 72 h at ≤25° C.

21. The pharmaceutical aqueous solution according to any one of the preceding embodiments, wherein said solution is produced at commercial scale manufacturing, in particular is produced at a batch size of at least 20 GBq, at least 50 GBq, or at least 70 GBq.

22a. The pharmaceutical aqueous solution according to any one of the preceding embodiments, which is ready-to-use.

22b. The pharmaceutical aqueous solution according to any one of the preceding embodiments, which is for commercial use.

23. A pharmaceutical aqueous solution, comprising
    (a) a complex formed by
       (ai) the radionuclide $^{177}$Lutetium (Lu-177), present in a concentration that it provides a volumetric radioactivity of from 250 to 500 MBq/mL, and
       (aii) the chelating agent linked somatostatin receptor binging organic moiety DOTA-TATE (oxodotreotide) or DOTA-TOC (edotreotide);
    (bi) gentisic acid or a salt thereof as the first stabilizer against radiolytic degradation present in a concentration of from 0.5 to 1 mg/mL;
    (bii) ascorbic acid or a salt thereof as the second stabilizer against radiolytic degradation present in a concentration of from 2.0 to 5.0 mg/mL.

24. The pharmaceutical aqueous solution according to embodiment 23, further comprising:
    (c) Diethylentriaminepentaacetic acid (DTPA) or a salt thereof in a concentration of from 0.01 to 0.10 mg/mL.

25. The pharmaceutical aqueous solution according to embodiments 23 or 24, further comprising:
    (d) acetic acid in a concentration of from 0.3 to 0.7 mg/mL and sodium acetate in a concentration from 0.4 to 0.9 mg/mL.

26. The pharmaceutical aqueous solution according to any one of the preceding embodiments wherein the stabilizer (s) is (are) present in the solution during the complex formation of components (ai) and (aii).

27. The pharmaceutical aqueous solution according to any one of embodiments 5 to 26 wherein only the first stabilizer is present during the complex formation of components (ai) and (aii), preferably in an amount to result in a concentration of from 0.5 to 5 mg/mL, more preferably from 0.5 to 2 mg/mL, even more preferably from 0.5 to 1 mg/mL, even more preferably from 0.5 to 0.7 mg/mL, in the final solution.

28. The pharmaceutical aqueous solution according to any one of embodiments 6 to 27 wherein a part of the amount of the second stabilizer is already present in the solution during the complex formation of components (ai) and (aii) and another part of the amount of the second stabilizer is added after the complex formation of components (ai) and (aii).

29. The pharmaceutical aqueous solution according to any one of embodiments 6 to 28 wherein the second stabilizer is added after the complex formation of components (ai) and (aii).

30. The pharmaceutical aqueous solution according to embodiment 6 or 29 wherein the second stabilizer is added after the complex formation of components (ai) and (aii), preferably in an amount to result in a concentration of from 0.5 to 10 mg/mL, more preferably from 1.0 to 8.0 mg/mL, even more preferably from 2.0 to 5.0 mg/mL, even more preferably from 2.2 to 3.4 mg/mL, in the final solution.

31. The pharmaceutical aqueous solution according to any one of the preceding embodiments, further comprising a sequestering agent, added after the complex formation of components (ai) and (aii), for removing any uncomplexed Lu, preferably said sequestering agent is diethylentriaminepentaacetic acid (DTPA) or a salt thereof, preferably in an amount to result in a concentration of from 0.01 to 0.10 mg/mL (preferably about 0.05 mg/mL) in the final solution.

32. A process for manufacturing the pharmaceutical aqueous solution as defined in any one of the preceding embodiments, comprising the process steps:
    (1) Forming a complex of the radionuclide and the chelating agent linked cell receptor binding organic moiety by
       (1.1) preparing an aqueous solution comprising the radionuclide;
       (1.2) preparing an aqueous solution comprising the chelating agent linked cell receptor binding organic moiety, a first stabilizer, optionally a second stabilizer; and
       (1.3) mixing the solutions obtained in steps (1.1) and (1.2) and heating the resulting mixture;
    (2) Diluting the complex solution obtained by step (1) by
       (2.1) preparing an aqueous dilution solution optionally comprising a second stabilizer; and
       (2.2.) mixing the complex solution obtained by step (1) with the dilution solution obtained by the step (2.1).

33. The process according to embodiment 32 wherein only the first stabilizer is present during the step (1.3), preferably in an amount to result in a concentration of from 0.5 to 5 mg/mL, more preferably from 0.5 to 2 mg/mL, even more preferably from 0.5 to 1 mg/mL, even more preferably from 0.5 to 0.7 mg/mL, in the final solution.

34. The process according to any one of embodiments 32 to 33 wherein a part of the amount of the second stabilizer is already present in the solution during the step (1.3) and another part of the amount of the second stabilizer is added, after the step (1.3), in step (2.1).

35. The pharmaceutical aqueous solution according to any one of embodiments 32 to 34 wherein the second stabilizer is added, after the step (1.3), in step (2.1).

36. The pharmaceutical aqueous solution according to any one of embodiments 32 to 35 wherein the second stabilizer is added, after the step (1.3), in step (2.1), preferably in an amount to result in a concentration of from 0.5 to 10 mg/mL, more preferably from 1.0 to 8.0 mg/mL, even more preferably from 2.0 to 5.0 mg/mL, even more preferably from 2.2 to 3.4 mg/mL, in the final solution.

37. The process according any one of embodiments 32 to 36, wherein the solution of step (1.2) further comprises a buffer, preferably an acetate buffer.

38. The process according to any one of embodiments 32 to 37, wherein in step (1.3) the resulting mixture is heated to a temperature of from 70 to 99° C., preferably from 90 to 98° C., for from 2 to 59 min.

39. The process according to any one of embodiments 32 to 38, wherein the solution of step (2.1) further comprises diethylentriaminepentaacetic acid (DTPA) or a salt thereof.

40. The process according to any one of embodiments 32 to 39, further comprising the process steps:

(3) Filtering the solution obtained by step (2) through 0.2 µm:

(4) Dispensing the filtered solution obtained by step (3) into dose unit containers in a volume required to deliver the radioactive dose of from 5.0 to 10 MBq, preferably from 7.0 to 8.0 MBq, more preferably from 7.3 to 7.7 MBq, even more preferably from 7.4-7.5 MBq, preferably said volume is from 10 to 50 mL, more preferably from 15 to 30 mL, even more preferably from 20 to 25 mL.

41. The process according to any one of embodiments 32 to 40, wherein the solution of step (1.1) comprises $LuCl_3$ and HCl.

42. The process according to any one of embodiments 32 to 41, wherein the solution of step (1.2) comprises $^{177}$Lu-DOTA-TATE or $^{177}$Lu-DOTA-TOC, gentisic acid, acetic acid, and sodium acetate.

43. The process according to any one of embodiments 32 to 42, wherein the solution of step (2.1) comprises DTPA, and ascorbic acid.

44. The process according to any one of embodiments 32 to 43, wherein the dose unit containers in step (4) are stoppered vials, enclosed within a lead container.

45. The pharmaceutical aqueous solution obtained (or obtainable) by the process as defined in any one of the embodiments 32 to 44.

Further embodiments of the present invention are described in the following as "E embodiments":

E1. A pharmaceutical aqueous solution comprising:
  (a) a complex formed by
    (ai) the radionuclide $^{177}$Lu (Lutetium-177), and
    (aii) a somatostatin receptor binding peptide linked to the chelating agent DOTA; and
  (b) at least two different stabilizers against radiolytic degradation;
  wherein
    said radionuclide is present in a concentration that it provides a volumetric radioactivity of from 250 to 500 MBq/mL; and
    said stabilizers are present in a total concentration of from 0.2 to 20.0 mg/mL.

The "complex formed by" may be alternatively worded: "complex of".

The "different" in "two different stabilizers" refers to a difference in the chemical entity of such stabilizers. "Two different stabilizers" has the meaning that the two stabilizers are different chemical entities, e.g. gentisic acid and ascorbic acid are two different stabilizers. "at least two" means two or more, however, preferably that just two stabilizers are present (not three or more). It is further preferred that ethanol is not one of the two stabilizers.

E2. The pharmaceutical aqueous solution according to embodiment E1,
  wherein said component (b) comprises the stabilizers:
    (bi) gentisic acid or a salt thereof; and
    (bii) ascorbic acid or a salt thereof.

E3. The pharmaceutical aqueous solution according to embodiment E2,
  wherein
    (bi) gentisic acid is present in a concentration of from 0.5 to 2 mg/mL, preferably from 0.5 to 1 mg/mL; and
    (bii) ascorbic acid is present in a concentration of from 2.0 to 5.0 mg/mL.

In a particular embodiment the present invention provides:
A pharmaceutical aqueous solution comprising:
  (a) a complex formed by
    (ai) the radionuclide $^{177}$Lu (Lutetium-177) in a concentration that it provides a volumetric radioactivity of from 250 to 500 MBq/mL, and
    (aii) a somatostatin receptor binding peptide linked to the chelating agent DOTA; and
  (b) the stabilizers against radiolytic degradation
    (bi) gentisic acid in a concentration of from 0.5 to 1 mg/mL and
    (bii) ascorbic acid in a concentration of from 2.0 to 5.0 mg/mL.

E4. The pharmaceutical aqueous solution according to embodiment E3, further comprising:
  (c) diethylentriaminepentaacetic acid (DTPA) or a salt thereof in a concentration of from 0.01 to 0.10 mg/mL.

E5. The pharmaceutical aqueous solution according to embodiments E3 or E4, further comprising:
  (d) an acetate buffer composed of:
    (di) acetic acid in a concentration of from 0.3 to 0.7 mg/mL; and
    (dii) sodium acetate in a concentration from 0.4 to 0.9 mg/mL;
  preferably said acetate buffer provides for a pH of from 4.5 to 6.0, preferably from 4.7 to 6.0, more preferably from 5.0 to 6.0, even more preferably from 5.0 to 5.5.

In a particular embodiment the present invention provides:
A pharmaceutical aqueous solution comprising:
  (a) a complex formed by
    (ai) the radionuclide $^{177}$Lu (Lutetium-177) in a concentration that it provides a volumetric radioactivity of from 250 to 500 MBq/mL, and
    (aii) a somatostatin receptor binding peptide linked to the chelating agent DOTA;
  (b) at least two stabilizers against radiolytic degradation comprising (bi) gentisic acid in a concentration of from 0.5 to 1 mg/mL and (bii) ascorbic acid in a concentration of from 2.0 to 5.0 mg/mL;
  (c) diethylentriaminepentaacetic acid (DTPA) or a salt thereof in a concentration of from 0.01 to 0.10 mg/mL; and
  (d) an acetate buffer composed of:
    (di) acetic acid in a concentration of from 0.3 to 0.7 mg/mL; and
    (dii) sodium acetate in a concentration from 0.4 to 0.9 mg/mL;
  preferably said acetate buffer provides for a pH of from 5.0 to 5.5.

In a particular embodiment the present invention provides:
A pharmaceutical aqueous solution comprising:
  (a) a complex formed by
    (ai) the radionuclide $^{177}$Lu (Lutetium-177) in a concentration that it provides a volumetric radioactivity of from 250 to 500 MBq/mL, and
    (aii) a somatostatin receptor binding peptide linked to the chelating agent DOTA;
  (b) stabilizers against radiolytic degradation consisting of (bi) gentisic acid in a concentration of from 0.5 to 1 mg/mL and (bii) ascorbic acid in a concentration of from 2.0 to 5.0 mg/mL;
  (c) diethylentriaminepentaacetic acid (DTPA) or a salt thereof in a concentration of from 0.01 to 0.10 mg/mL; and (d) an acetate buffer composed of:
  (di) acetic acid in a concentration of from 0.3 to 0.7 mg/mL; and
  (dii) sodium acetate in a concentration from 0.4 to 0.9 mg/mL;
preferably said acetate buffer provides for a pH of from 5.0 to 5.5.

The herein indicated pH values are the pH values of the final solution. However, it can also be the pH during manufacturing of the solution, e.g. the pH during the complex formation.

E6. The pharmaceutical aqueous solution according to any one of the embodiments E1 to E5 wherein at least one of the stabilizers is present during the complex formation of components (ai) and (aii) and at least one of the stabilizers is added after the complex formation of components (ai) and (aii).

E7. The pharmaceutical aqueous solution according to any one of the embodiments E1 to E5 wherein at least gentisic acid is present during the complex formation of components (ai) and (aii) and at least ascorbic acid is added after the complex formation of components (ai) and (aii).

E8. The pharmaceutical aqueous solution according to any one of the embodiments E1 to E5 wherein the only stabilizer present during the complex formation of components (ai) and (aii) is gentisic acid and the only stabilizer added after the complex formation of components (ai) and (aii) is ascorbic acid.

In a particular embodiment the present invention provides:

A pharmaceutical aqueous solution comprising:
(a) a complex formed by
  (ai) the radionuclide $^{177}$Lu (Lutetium-177) in a concentration that it provides a volumetric radioactivity of from 250 to 500 MBq/mL, and
  (aii) a somatostatin receptor binding peptide linked to the chelating agent DOTA; and
(b) the stabilizers against radiolytic degradation
  (bi) gentisic acid in a concentration of from 0.5 to 1 mg/mL (in the final solution) and
  (bii) ascorbic acid in a concentration of from 2.0 to 5.0 mg/mL (in the final solution);
wherein gentisic acid is present during the complex formation of components (ai) and (aii) and ascorbic acid added after the complex formation of components (ai) and (aii).

In a particular embodiment the present invention is defined in the following:

A pharmaceutical aqueous solution comprising:
(a) a complex formed by
  (ai) the radionuclide $^{177}$Lu (Lutetium-177) in a concentration that it provides a volumetric radioactivity of from 250 to 500 MBq/mL, and
  (aii) a somatostatin receptor binding peptide linked to the chelating agent DOTA;
(b) at least two stabilizers against radiolytic degradation comprising (bi) gentisic acid in a concentration of from 0.5 to 1 mg/mL and (bii) ascorbic acid in a concentration of from 2.0 to 5.0 mg/mL;
(c) diethylentriaminepentaacetic acid (DTPA) or a salt thereof in a concentration of from 0.01 to 0.10 mg/mL; and
(d) an acetate buffer composed of:
  (di) acetic acid in a concentration of from 0.3 to 0.7 mg/mL; and
  (dii) sodium acetate in a concentration from 0.4 to 0.9 mg/mL;
preferably said acetate buffer provides for a pH of from 5.0 to 5.5;
wherein gentisic acid is present during the complex formation of components (ai) and (aii) and ascorbic acid added after the complex formation of components (ai) and (aii).

In a particular embodiment the present invention is defined in the following:

A pharmaceutical aqueous solution comprising:
(a) a complex formed by
  (ai) the radionuclide $^{177}$Lu (Lutetium-177) in a concentration that it provides a volumetric radioactivity of from 250 to 500 MBq/mL, and
  (aii) a somatostatin receptor binding peptide linked to the chelating agent DOTA;
(b) stabilizers against radiolytic degradation consisting of (bi) gentisic acid in a concentration of from 0.5 to 1 mg/mL and (bii) ascorbic acid in a concentration of from 2.0 to 5.0 mg/mL;
(c) diethylentriaminepentaacetic acid (DTPA) or a salt thereof in a concentration of from 0.01 to 0.10 mg/mL; and
(d) an acetate buffer composed of:
  (di) acetic acid in a concentration of from 0.3 to 0.7 mg/mL; and
  (dii) sodium acetate in a concentration from 0.4 to 0.9 mg/mL;
preferably said acetate buffer provides for a pH of from 5.0 to 5.5;
wherein gentisic acid is present during the complex formation of components (ai) and (aii) and ascorbic acid added after the complex formation of components (ai) and (aii).

E9. The pharmaceutical aqueous solution according to any one of the embodiments E6 to E8 wherein that/those stabilizer/stabilizers which is/are present during the complex formation of components (ai) and (aii) is/are present during the complex formulation in a total concentration of from 15 to 50 mg/mL, preferably from 20 to 40 mg/mL.

E10. The pharmaceutical aqueous solution according to embodiment E9 wherein the only stabilizer present during the complex formation of components (ai) and (aii) is gentisic acid and is present during the complex formulation in a concentration of from 20 to 40 mg/mL, preferably from 25 to 35 mg/mL.

In a particular embodiment the present invention is defined in the following:

A pharmaceutical aqueous solution comprising:
(a) a complex formed by
  (ai) the radionuclide $^{177}$Lu (Lutetium-177) in a concentration that it provides a volumetric radioactivity of from 250 to 500 MBq/mL, and
  (aii) a somatostatin receptor binding peptide linked to the chelating agent DOTA;
(b) at least two stabilizers against radiolytic degradation comprising (bi) gentisic acid in a concentration of from 0.5 to 1 mg/mL and (bii) ascorbic acid in a concentration of from 2.0 to 5.0 mg/mL;
(c) diethylentriaminepentaacetic acid (DTPA) or a salt thereof in a concentration of from 0.01 to 0.10 mg/mL; and
(d) an acetate buffer composed of:
  (di) acetic acid in a concentration of from 0.3 to 0.7 mg/mL; and
  (dii) sodium acetate in a concentration from 0.4 to 0.9 mg/mL;

preferably said acetate buffer provides for a pH of from 5.0 to 5.5;

wherein gentisic acid is present during the complex formation of components (ai) and (aii) and ascorbic acid added after the complex formation of components (ai) and (aii); and wherein the only stabilizer present during the complex formation of components (ai) and (aii) is gentisic acid and is present during the complex formulation in a concentration of from 20 to 40 mg/mL, preferably from 25 to 35 mg/mL.

In a particular embodiment the present invention is defined in the following:

A pharmaceutical aqueous solution comprising:
(a) a complex formed by
   (ai) the radionuclide $^{177}$Lu (Lutetium-177) in a concentration that it provides a volumetric radioactivity of from 250 to 500 MBq/mL, and
   (aii) a somatostatin receptor binding peptide linked to the chelating agent DOTA;
(b) stabilizers against radiolytic degradation consisting of (bi) gentisic acid in a concentration of from 0.5 to 1 mg/mL and (bii) ascorbic acid in a concentration of from 2.0 to 5.0 mg/mL;
(c) diethylentriaminepentaacetic acid (DTPA) or a salt thereof in a concentration of from 0.01 to 0.10 mg/mL; and
(d) an acetate buffer composed of:
   (di) acetic acid in a concentration of from 0.3 to 0.7 mg/mL; and
   (dii) sodium acetate in a concentration from 0.4 to 0.9 mg/mL;
preferably said acetate buffer provides for a pH of from 5.0 to 5.5;

wherein gentisic acid is present during the complex formation of components (ai) and (aii) and ascorbic acid added after the complex formation of components (ai) and (aii); and wherein the only stabilizer present during the complex formation of components (ai) and (aii) is gentisic acid and is present during the complex formulation in a concentration of from 20 to 40 mg/mL, preferably from 25 to 35 mg/mL.

Embodiments E6 to E10 may be alternatively defined by the following wording:

E6. The pharmaceutical aqueous solution according to any one of the embodiments E1 to E5 produced by having at least one of the stabilizers present during the complex formation of components (ai) and (aii) and at least one of the stabilizers added after the complex formation of components (ai) and (aii).

E7. The pharmaceutical aqueous solution according to any one of the embodiments E1 to E5 produced by having at least gentisic acid present during the complex formation of components (ai) and (aii) and at least ascorbic acid added after the complex formation of components (ai) and (aii).

E8. The pharmaceutical aqueous solution according to any one of the embodiments E1 to E5 produced by having gentisic acid as the only stabilizer present during the complex formation of components (ai) and (aii) ascorbic acid as the only stabilizer added after the complex formation of components (ai) and (aii).

E9. The pharmaceutical aqueous solution according to any one of the embodiments E6 to E8 produced by having that/those stabilizer/stabilizers present during the complex formation of components (ai) and (aii) present during the complex formation in a total concentration of from 15 to 50 mg/mL, preferably from 20 to 40 mg/mL.

E10. The pharmaceutical aqueous solution according to embodiment E9 produced by having gentisic acid as the only stabilizer present during the complex formation of components (ai) and (aii) and present during the complex formulation in a concentration of from 20 to 40 mg/mL, preferably from 25 to 35 mg/mL.

In the embodiments of the present invention, in particular in embodiments E9 and E10, the radionuclide may be present during the complex formation in a concentration that it provides a volumetric radioactivity of up to 20 GBq/mL, preferably up to 15 GBq/mL, or from 5 to 20 GBq/mL, preferably from 10 to 20 GBq/mL, more preferably from 10 to 15 GBq/mL.

In a particular embodiment the present invention is defined in the following:

A pharmaceutical aqueous solution comprising:
(a) a complex formed by
   (ai) the radionuclide $^{177}$Lu (Lutetium-177) in a concentration that it provides a volumetric radioactivity of from 250 to 500 MBq/mL (in the final solution), and
   (aii) a somatostatin receptor binding peptide linked to the chelating agent DOTA;
(b) at least two stabilizers against radiolytic degradation comprising (bi) gentisic acid in a concentration of from 0.5 to 1 mg/mL and (bii) ascorbic acid in a concentration of from 2.0 to 5.0 mg/mL;
(c) diethylentriaminepentaacetic acid (DTPA) or a salt thereof in a concentration of from 0.01 to 0.10 mg/mL; and
(d) an acetate buffer composed of:
   (di) acetic acid in a concentration of from 0.3 to 0.7 mg/mL; and
   (dii) sodium acetate in a concentration from 0.4 to 0.9 mg/mL;
preferably said acetate buffer provides for a pH of from 5.0 to 5.5;

wherein gentisic acid is present during the complex formation of components (ai) and (aii) and ascorbic acid added after the complex formation of components (ai) and (aii); and wherein the only stabilizer present during the complex formation of components (ai) and (aii) is gentisic acid and is present during the complex formulation in a concentration of from 20 to 40 mg/mL;

and wherein the radionuclide is present during the complex formation in a concentration that it provides a volumetric radioactivity of from 10 to 20 GBq/mL.

In a particular embodiment the present invention is defined in the following:

A pharmaceutical aqueous solution comprising:
(a) a complex formed by
   (ai) the radionuclide $^{177}$Lu (Lutetium-177) in a concentration that it provides a volumetric radioactivity of from 250 to 500 MBq/mL (in the final solution), and
   (aii) a somatostatin receptor binding peptide linked to the chelating agent DOTA;
(b) stabilizers against radiolytic degradation consisting of (bi) gentisic acid in a concentration of from 0.5 to 1 mg/mL and (bii) ascorbic acid in a concentration of from 2.0 to 5.0 mg/mL;

(c) diethylentriaminepentaacetic acid (DTPA) or a salt thereof in a concentration of from 0.01 to 0.10 mg/mL; and
(d) an acetate buffer composed of:
   (di) acetic acid in a concentration of from 0.3 to 0.7 mg/mL; and
   (dii) sodium acetate in a concentration from 0.4 to 0.9 mg/mL;
preferably said acetate buffer provides for a pH of from 5.0 to 5.5;
wherein gentisic acid is present during the complex formation of components (ai) and (aii) and ascorbic acid added after the complex formation of components (ai) and (aii); and
wherein the only stabilizer present during the complex formation of components (ai) and (aii) is gentisic acid and is present during the complex formulation in a concentration of from 20 to 40 mg/mL;
and wherein the radionuclide is present during the complex formation in a concentration that it provides a volumetric radioactivity of from 10 to 20 GBq/mL.

E11. The pharmaceutical aqueous solution according to any one of the preceding E embodiments, which has a shelf life of at least 72 h when stored at ≤25° C., in particular at least 72 h when stored at 25° C.
   "Shelf life" has herein its general meaning in the context of pharmaceutical products. The shelf life is the length of time that a pharmaceutical product may be stored while its product characteristics still comply with the product specification as defined during drug development and agreed by health authorities.

E12. The pharmaceutical aqueous solution according to any one of the preceding E embodiments, for which the radiochemical purity (determined by HPLC) is maintained at ≥95% for at least 72 h when stored at 25° C.

E13. The pharmaceutical aqueous solution according to any one of the preceding E embodiments, wherein said solution is produced at commercial manufacturing scale, in particular is produced at a batch size of at least 20 GBq, at least 50 GBq, or at least 70 GBq.

E14. The pharmaceutical aqueous solution according to any one of the preceding embodiments, which is ready-to-use.

E15. A process for manufacturing the pharmaceutical aqueous solution as defined in any one of the preceding E embodiments, comprising the process steps:
   (1) Forming a complex of the radionuclide $^{177}$Lu and a somatostatin receptor binding peptide linked to the chelating agent DOTA by
      (1.1) preparing an aqueous solution comprising the radionuclide;
      (1.2) preparing an aqueous solution comprising the a somatostatin receptor binding peptide linked to the chelating agent, and at least one stabilizer against radiolytic degradation; and
      (1.3) mixing the solutions obtained in steps (1.1) and (1.2) and heating the resulting mixture;
   (2) Diluting the complex solution obtained by step (1) by
      (2.1) preparing an aqueous dilution solution optionally comprising at least one stabilizer against radiolytic degradation; and
      (2.2.) mixing the complex solution obtained by step (1) with the dilution solution obtained by the step (2.1) to obtain the final solution;
   wherein if the solution prepared under (1.2) comprises only one stabilizer, then the solution prepared under (2.1) comprise at least one stabilizer.

E16. The process according to embodiment E15 wherein the solution prepared in step (1.2) comprises at least one stabilizer and the solution prepared in step (2.1) comprises at least one stabilizer.

E17. The process according to embodiment E15 wherein the solution prepared in step (1.2) comprises at least the stabilizer gentisic acid and the solution prepared in step (2.1) comprises at least the stabilizer ascorbic acid.

E18. The process according to embodiment E15 wherein the solution prepared in step (1.2) comprises only one stabilizer which is gentisic acid and the solution prepared in step (2.1) comprises only one stabilizer which is ascorbic acid.

E19. The process according to any one of embodiments E15 to E18 wherein the solution prepared in step (1.2) comprises stabilizer/stabilizers in a total concentration of from 15 to 50 mg/mL, preferably from 20 to 40 mg/mL.

E20. The process according to any one of embodiments E15 to E18 wherein the solution prepared in step (1.2) comprises only one stabilizer which is gentisic acid in a concentration of from 20 to 40 mg/mL, preferably from 25 to 35 mg/mL.

E21. The process according any one of embodiments E15 to E20, wherein the solution of step (1.2) further comprises a buffer, preferably an acetate buffer.

E22. The process according to any one of embodiments E15 to E21, wherein in step (1.3) the resulting mixture is heated to a temperature of from 70 to 99° C. (e.g., between 80-99° C.), preferably from 90 to 98° C. (e.g., 90-95° C.), for from 2 to 59 min (e.g., 2-20 min, 2-15 min, 5-15 min, or 5-12 min), preferably from 5-15 min or 10 to 15 min.

E23. The process according to any one of embodiments E15 to E22, wherein the solution of step (2.1) further comprises diethylentriaminepentaacetic acid (DTPA) or a salt thereof.

E24. The process according to any one of embodiments E15 to E23, further comprising the process steps:
   (3) Filtering the solution obtained by step (2) through 0.2 µm:
   (4) Dispensing the filtered solution obtained by step (3) into dose unit containers in a volume required to deliver the radioactive dose of from 5.0 to 10 MBq, preferably from 7.0 to 8.0 MBq, more preferably from 7.3 to 7.7 MBq, even more preferably from 7.4-7.5 MBq, preferably said volume is from 10 to 50 mL, more preferably from 15 to 30 mL, even more preferably from 20 to 25 mL.

E25. The process according to any one of embodiments E15 to E24, wherein the solution of step (1.1) comprises LuCl$_3$ and HCl.

E26. The process according to any one of embodiments E15 to E25, wherein the solution of step (1.2) comprises $^{177}$Lu-DOTA-TATE or $^{177}$Lu-DOTA-TOC, gentisic acid, acetic acid, and sodium acetate.

E27. The process according to any one of embodiments E15 to E26, wherein the solution of step (2.1) comprises DTPA, and ascorbic acid.

E28. The process according to any one of embodiments E24 to E27, wherein the dose unit containers in step (4) are stoppered vials, enclosed within a lead container.

E29. The pharmaceutical aqueous solution obtained (or: obtainable) by the process as defined by any one of embodiments E15 to E28.

Further embodiments of the present invention are described in the following as "EE embodiments":

EE1. A process for manufacturing a pharmaceutical aqueous solution, comprising:
providing a solution comprising a complex of the radionuclide $^{177}$Lu (Lutetium-177) and a somatostatin receptor binding peptide linked to the chelating agent DOTA; a first stabilizer against radiolytic degradation, and optionally a second stabilizer against radiolytic degradation different from the first stabilizer; and
diluting the solution comprising the complex with an aqueous dilution solution optionally comprising at least one stabilizer against radiolytic degradation to obtain the pharmaceutical aqueous solution;
wherein if the solution comprising the complex comprises only the first stabilizer and not the second stabilizer, then the aqueous dilution solution comprises at least one stabilizer that is different from the first stabilizer, and in the obtained pharmaceutical aqueous solution, the radionuclide $^{177}$Lu is present in a concentration that it provides a volumetric radioactivity of from 250 to 500 MBq/mL and the stabilizers are present in a total concentration of from 0.2 to 20.0 mg/mL.
For example, the first stabilizer is gentisic acid or a salt thereof and the second stabilizer, when present, is ascorbic acid or a salt thereof. For example, the at least one stabilizer in the aqueous dilution solution, when present, is ascorbic acid or a salt thereof.

EE2. The process according to embodiment EE 1, comprising the process steps:
(1) forming a complex of the radionuclide $^{177}$Lu and a somatostatin receptor binding peptide linked to the chelating agent DOTA by
(1.1) providing an aqueous solution comprising the radionuclide;
(1.2) providing an aqueous solution comprising the a somatostatin receptor binding peptide linked to the chelating agent, and a first stabilizer against radiolytic degradation and optionally a second stabilizer against radiolytic degradation different from the first stabilizer; and
(1.3) mixing the solutions provided in steps (1.1) and (1.2) and heating the resulting mixture to form a solution comprising the complex;
(2) diluting the solution comprising the complex obtained by step (1) by
(2.1) providing an aqueous dilution solution optionally comprising at least one stabilizer against radiolytic degradation; and
(2.2.) mixing the solution comprising the complex obtained by step (1) with the dilution solution provided in step (2.1) to obtain the pharmaceutical aqueous solution;
wherein if the solution in step (1.2) comprises only one stabilizer that is the first stabilizer, then the solution in step (2.1) comprise at least one stabilizer that is different from the first stabilizer.

EE3. The process according to embodiment EE1 or EE2, wherein the solution in step (1.2) comprises the first stabilizer and the solution provided in step (2.1) comprises at least one stabilizer.

EE4. The process according to any one of embodiments EE1 to EE3, wherein the solution provided in step (1.2) comprises at least gentisic acid or a salt thereof and the solution provided in step (2.1) comprises at least ascorbic acid or a salt thereof.

EE5. The process according to any one of embodiments EE1 to EE4, wherein the solution provided in step (1.2) comprises only one stabilizer which is gentisic acid or a salt thereof and the solution provided in step (2.1) comprises only one stabilizer which is ascorbic acid or a salt thereof.

EE6. The process according to any one of embodiments EE1 to EE5, wherein the solution provided in step (1.2) comprises stabilizer/stabilizers in a total concentration of from 15 to 50 mg/mL.

EE7. The process according to any one of embodiments EE1 to EE6, wherein the solution provided in step (1.2) comprises stabilizer/stabilizers in a total concentration of from 20 to 40 mg/mL EE8. The process according to any one of embodiments EE1 to EE7, wherein the solution provided in step (1.2) comprises only one stabilizer which is gentisic acid in a concentration of from 20 to 40 mg/mL.

EE9. The process according to any one of embodiments EE1 to EE8, wherein the solution provided in step (1.2) comprises only one stabilizer which is gentisic acid in a concentration of from 25 to 35 mg/mL.

EE10. The process according to any one of embodiments EE1 to EE9, wherein the solution provided in step (1.2) further comprises a buffer, e.g., an acetate buffer.

EE11. The process according to any one of embodiments EE1 to EE10, wherein in step (1.3) the resulting mixture is heated to a temperature of from 70 to 99° C. (e.g., between 80-99° C., 90-98° C., or between 90-95° C.).

EE12. The process according to any one of embodiments EE1 to EE11, wherein in step (1.3) the resulting mixture is heated from 2 to 59 min (e.g., 2-20 min, 2-15 min, 5-15 min, 5-12 min, 5-15 min or 10 to 15 min).

EE13. The process according to any one of embodiments EE1 to EE12, wherein in step (1.3) the resulting mixture is heated to a temperature of from 90 to 98° C. for from 10 to 15 min.

EE14. The process according to any one of embodiments EE1 to EE13, wherein the solution provided in step (2.1) further comprises diethylentriaminepentaacetic acid (DTPA) or a salt thereof.

EE15. The process according to any one of embodiments EE1 to EE14, further comprising the process steps:
(3) filtering the solution obtained by step (2) through 0.2 μm; and
(4) dispensing the filtered solution obtained by step (3) into dose unit containers in a volume required to deliver the radioactive dose of from about 5 to about 10 MBq (e.g., from about 7 to about 8 MBq, or from 7.3 to 7.7 MBq, or from 7.4-7.5 MBq).

For example, the volume in embodiment EE15 is from about 10 to about 50 mL, e.g., from about 15 to about 30 mL or from about 20 to about 25 mL.

EE16. The process according to any one of embodiments EE1 to EE15, wherein the solution of step (1.1) comprises LuCl$_3$ and HCl.

EE17. The process according to any one of embodiments EE1 to EE16, wherein the solution of step (1.2) comprises $^{177}$Lu-DOTA-TATE or $^{177}$Lu-DOTA-TOC, gentisic acid, acetic acid, and sodium acetate.

EE18. The process according to any one of embodiments EE1 to EE17, wherein the solution of step (2.1) comprises DTPA and ascorbic acid.

EE19. The process according to any one of embodiments EE15 to EE18, wherein the dose unit containers in step (4) are stoppered vials, enclosed within a lead container.

EE20. The pharmaceutical aqueous solution obtained (or: obtainable) by the process as defined by any one of embodiments EE1 to E19.

EE21. The pharmaceutical aqueous solution according to embodiment EE20, which has a shelf life of at least 72 h when stored at 25° C., in particular at least 72 h when stored at 25° C.

EE22. The pharmaceutical aqueous solution according to embodiment EE20 or EE21, for which the radiochemical purity (determined by HPLC) is maintained at ≥95% for at least 72 h when stored at 25° C.

EE23. The pharmaceutical aqueous solution according to any one of embodiments EE20 to EE22, wherein said solution is produced at a batch size of at least 20 GBq, at least 50 GBq, or at least 70 GBq.

EE24. The pharmaceutical aqueous solution according to any one of embodiments EE20 to EE23, which is ready to use.

EE25. The pharmaceutical aqueous solution according to any one of embodiments EE20 to EE24, free of ethanol.

EE26. The pharmaceutical aqueous solution according to any one of embodiments EE20 to EE25, wherein gentisic acid is present in a concentration of from 0.5 to 2 mg/mL, preferably from 0.5 to 1 mg/mL; and ascorbic acid is present in a concentration of from 2.0 to 5.0 mg/mL.

EE27. The pharmaceutical aqueous solution according to any one of embodiments EE20 to EE26, wherein the diethylentriaminepentaacetic acid (DTPA) or a salt thereof is present in a concentration of from 0.01 to 0.10 mg/mL.

EE28. The pharmaceutical aqueous solution according to any one of embodiments EE20 to EE27, wherein the acetate buffer is composed of acetic acid in a concentration of from 0.3 to 0.7 mg/mL; and sodium acetate in a concentration from 0.4 to 0.9 mg/mL; preferably said acetate buffer provides for a pH of from 4.5 to 6.0, preferably from 5.0 to 5.5.

In all the embodiments as described herein, the somatostatin receptor binding peptide linked to the chelating agent DOTA (component (aii)) is preferably DOTA-TATE (oxodotreotide) or DOTA-TOC (edotreotide), more preferably DOTA-TATE (oxodotreotide).

The present invention further provides the pharmaceutical aqueous solution as defined herein for use in the treatment of neuroendocrine tumors (NET).

Alternatively, the present invention provides a method for the treatment of NET in human patients in need of such treatment which comprises administering an effective amount of the pharmaceutical aqueous solution as defined herein.

As a further alternative the present invention provides the use of pharmaceutical aqueous solution as defined herein for the manufacture/preparation of a medicament for the treatment of NET.

As a further alternative the present invention provides a medicament for the treatment of NET comprising pharmaceutical aqueous solution as defined herein.

Neuroendocrine tumors (NET) which may be treated by the pharmaceutical aqueous solutions as defined here alone or in combinations in accordance with the present invention are selected from the group consisting of gastroenteropancreatic neuroendocrine tumor, carcinoid tumor, pheochromocytoma, paraganglioma, medullary thyroid cancer, pulmonary neuroendocrine tumor, thymic neuroendocrine tumor, a carcinoid tumor or a pancreatic neuroendocrine tumor, pituitary adenoma, adrenal gland tumors, Merkel cell carcinoma, breast cancer, Non-Hodgkin lymphoma, Hodgkin lymphoma, Head & Neck tumor, urothelial carcinoma (bladder), Renal Cell Carcinoma, Hepatocellular Carcinoma, GIST, neuroblastoma, bile duct tumor, cervix tumor, Ewing sarcoma, osteosarcoma, small cell lung cancer (SCLC), prostate cancer, melanoma, meningioma, glioma, medulloblastoma, hemangioblastoma, supratentorial primitive, neuroectodermal tumor, and esthesioneuroblastoma.

Further NET tumors which may be treated by the pharmaceutical aqueous solutions as defined here alone or in combinations in accordance with the present invention may be selected from the group consisting of functional carcinoid tumor, insulinoma, gastrinoma, vasoactive intestinal peptide (VIP) oma, glucagonoma, serotoninoma, histaminoma, ACTHoma, pheocromocytoma, and somatostatinoma.

The present invention further provides the combination or combination therapy of the complex formed by the radionuclide $^{177}$Lu (Lutetium-177), and a somatostatin receptor binding peptide linked to the chelating agent as defined herein, or the combination or combination therapy of the pharmaceutical aqueous solution as defined herein, together with one of more therapeutic agents as outlined in the following:

In certain instances, pharmaceutical aqueous solution of the present invention are combined with other therapeutic agents, such as other anti-cancer agents, anti-allergic agents, anti-nausea agents (or anti-emetics), pain relievers, cytoprotective agents, and combinations thereof.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with the pharmaceutical aqueous solution of the present invention include:

Tyrosine kinase inhibitors: Erlotinib hydrochloride (Tarceva®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); and Imatinib or Imatinib mesylate (Gilvec® and Gleevec®).

Vascular Endothelial Growth Factor (VEGF) receptor inhibitors: Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®), sulfatinib, surufatinib.

Platelet-derived Growth Factor (PDGF) receptor inhibitors: Imatinib (Gleevec®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Quizartinib (AC220, CAS 950769-58-1); Pazopanib (Votrient®); Axitinib (Inlyta®); Sorafenib (Nexavar®); Vargatef (BIBF1120, CAS 928326-83-4); Telatinib (BAY57-9352, CAS 332012-40-5); Vatalanib dihydrochloride (PTK787, CAS 212141-51-0); and Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470).

Fibroblast Growth Factor Receptor (FGFR) Inhibitors: Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Vargatef (BIBF1120, CAS 928326-83-4); Dovitinib dilactic acid (TKI258, CAS 852433-84-2); 3-(2,6-Dichloro-3,5-dimethoxy-phenyl)-1-{6-[4-(4-ethyl-piperazin-1-yl)-phenylamino]-pyrimidin-4-yl}-1-methyl-urea (BGJ398, CAS 872511-34-7); Danusertib (PHA-739358); and N-[2-[[4-(Diethylamino)butyl]amino]-6-(3,5-dimethoxyphenyl)pyrido[2,3-d]pyrimidin-7-yl]-N'-(1,1-dimethylethyl)-urea (PD173074, CAS 219580-11-7). sulfatinib, surufatinib.

Aurora kinase inhibitors: Danusertib (PHA-739358); N-[4-[[6-Methoxy-7-[3-(4-morpholinyl)propoxy]-4-quinazolinyl]amino]phenyl]benzamide (ZM447439, CAS 331771-20-1); 4-(2-Amino-4-methyl-5-thiazolyl)-N-[4-(4-morpholinyl)phenyl]-2-pyrimidinamine (CYC116, CAS 693228-63-6); Tozasertib (VX680 or MK-0457, CAS 639089-54-6); Alisertib (MLN8237); (N-{2-[6-(4-Cyclobutylamino-5-trifluoromethyl-pyrimidine-2-ylamino)-(1S,4R)-1,2,3,4-tetrahydro-1,4-epiazano-naphthalen-9-yl]-2-oxo-ethyl}-acetamide) (PF-03814735); 4-[[9-Chloro-7-(2,6-difluorophenyl)-5H-pyrimido[5,4-d][2]benzazepin-2-yl]amino]-benzoic acid (MLN8054, CAS 869363-13-3); Cenisertib (R-763); Barasertib (AZD1152); and N-cyclopropyl-N'-[3-[6-(4-morpholinylmethyl)-1H-benzimidazol-2-yl]-1H-pyrazol-4-yl]-urea (AT9283).

Cyclin-Dependent Kinase (CDK) inhibitors: Aloisine A; Alvocidib (also known as flavopiridol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002); Crizotinib (PF-02341066, CAS 877399-52-5); 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00, CAS 920113-03-7); Indisulam (E7070); Roscovitine (CYC202); 6-Acetyl-8-cyclopentyl-5-methyl-2-(5-piperazin-1-yl-pyridin-2-ylamino)-8H-pyrido[2,3-d]pyrimidin-7-one, hydrochloride (PD0332991); Dinaciclib (SCH727965); N-[5-[[(5-tert-Butyloxazol-2-yl)methyl]thio]thiazol-2-yl]piperidine-4-carboxamide (BMS 387032, CAS 345627-80-7); 4-[[9-Chloro-7-(2,6-difluorophenyl)-5H-pyrimido[5,4-d][2]benzazepin-2-yl]amino]-benzoic acid (MLN8054, CAS 869363-13-3); 5-[3-(4,6-Difluoro-1H-benzimidazol-2-yl)-1H-indazol-5-yl]-N-ethyl-4-methyl-3-pyridinemethanamine (AG-024322, CAS 837364-57-5); 4-(2,6-Dichlorobenzoylamino)-1H-pyrazole-3-carboxylic acid N-(piperidin-4-yl) amide (AT7519, CAS 844442-38-2); 4-[2-Methyl-1-(1-methylethyl)-1H-imidazol-5-yl]-N-[4-(methylsulfonyl)phenyl]-2-pyrimidinamine (AZD5438, CAS 602306-29-6); Palbociclib (PD-0332991); and (2R,3R)-3-[[2-[[3-[[S(R)]—S-cyclopropylsulfonimidoyl]-phenyl]amino]-5-(trifluoromethyl)-4-pyrimidinyl]oxy]-2-butanol (BAY 10000394), ribociclib.

Checkpoint Kinase (CHK) inhibitors: 7-Hydroxystaurosporine (UCN-01); 6-Bromo-3-(1-methyl-1H-pyrazol-4-yl)-5-(3R)-3-piperidinyl-pyrazolo[1,5-a]pyrimidin-7-amine (SCH900776, CAS 891494-63-6); 5-(3-Fluorophenyl)-3-ureidothiophene-2-carboxylic acid N—[(S)-piperidin-3-yl] amide (AZD7762, CAS 860352-01-8); 4-[(3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(25)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (YGRKKRRQR-RRLYRSPAMPENL), and CBP501 ((d-Bpa)sws(d-Phe-F5)(d-Cha)rrrqrr); and (αR)-α-amino-N-[5,6-dihydro-2-(1-methyl-1H-pyrazol-4-yl)-6-oxo-1H-pyrrolo[4,3,2-ef][2,3]benzodiazepin-8-yl]-Cyclohexaneacetamide (PF-0477736).

3-Phosphoinositide-dependent kinase-1 (PDK1 or PDPK1) inhibitors: 7-2-Amino-N-[4-[5-(2-phenanthrenyl)-3-(trifluoromethyl)-1H-pyrazol-1-yl]phenyl]-acetamide (OSU-03012, CAS 742112-33-0); Pyrrolidine-1-carboxylic acid (3-{5-bromo-4-[2-(1H-imidazol-4-yl)-ethylamino]-pyrimidin-2-ylamino}-phenyl)-amide (BX912, CAS 702674-56-4); and 4-Dodecyl-N-1,3,4-thiadiazol-2-yl-benzenesulfonamide (PHT-427, CAS 1191951-57-1).

Protein Kinase C (PKC) activators: Bryostatin I (bryo-1) and Sotrastaurin (AEB071).

B-RAF inhibitors: Regorafenib (BAY73-4506, CAS 755037-03-7); Tuvizanib (AV951, CAS 475108-18-0); Vemurafenib (Zelboraf®, PLX-4032, CAS 918504-65-1); 5-[1-(2-Hydroxyethyl)-3-(pyridin-4-yl)-1H-pyrazol-4-yl]-2, 3-dihydroinden-1-one oxime (GDC-0879, CAS 905281-76-7); 5-[2-[4-[2-(Dimethylamino)ethoxy]phenyl]-5-(4-pyridinyl)-1H-imidazol-4-yl]-2,3-dihydro-1H-Inden-1-one oxime (GSK2118436 or SB590885); (+/−)-Methyl (5-(2-(5-chloro-2-methylphenyl)-1-hydroxy-3-oxo-2,3-dihydro-1H-isoindol-1-yl)-1H-benzimidazol-2-yl)carbamate (also known as XL-281 and BMS908662) and N-(3-(5-chloro-1H-pyrrolo[2,3-b]pyridine-3-carbonyl)-2,4-difluorophenyl)propane-1-sulfonamide (also known as PLX4720).

C-RAF Inhibitors: Sorafenib (Nexavar®); 3-(Dimethylamino)-N-[3-[(4-hydroxybenzoyl)amino]-4-methylphenyl]-benzamide (ZM336372, CAS 208260-29-1); and 3-(1-cyano-1-methylethyl)-N-[3-[(3,4-dihydro-3-methyl-4-oxo-6-quinazolinyl)amino]-4-methylphenyl]-benzamide (AZ628, CAS 1007871-84-2).

Human Granulocyte colony-stimulating factor (G-CSF) modulators: Filgrastim (Neupogen®); Sunitinib malate (Sutent®); Pegilgrastim (Neulasta®) and Quizartinib (AC220, CAS 950769-58-1).

RET Inhibitors: Sunitinib malate (Sutent®); Vandetanib (Caprelsa®); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Sorafenib (BAY 43-9006); Regorafenib (BAY73-4506, CAS 755037-03-7); and Danusertib (PHA-739358).

FMS-like Tyrosine kinase 3 (FLT3) Inhibitors or CD135: Sunitinib malate (Sutent®); Quizartinib (AC220, CAS 950769-58-1); N-[(1-Methyl-4-piperidinyl)methyl]-3-[3-(trifluoromethoxy)phenyl]-Imidazo[1,2-b]pyridazin-6-amine sulfate (SG1-1776, CAS 1173928-26-1); and Vargatef (BIBF1120, CAS 928326-83-4).

c-KIT Inhibitors: Pazopanib (Votrient®); Dovitinib dilactic acid (TKI258, CAS 852433-84-2); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Masitinib (Masivet®); Regorafenib (BAY73-4506, CAS 755037-03-7); Tivozanib (AV951, CAS 475108-18-0); Vatalanib dihydrochloride (PTK787, CAS 212141-51-0); Telatinib (BAY57-9352, CAS 332012-40-5); Foretinib (GSK1363089, formerly XL880, CAS 849217-64-7); Sunitinib malate (Sutent®); Quizartinib (AC220, CAS 950769-58-1); Axitinib (Inlyta®); Dasatinib (BMS-345825); and Sorafenib (Nexavar®).

Bcr/Abl kinase inhibitors: Imatinib (Gleevec®); Inilotinib hydrochloride; Nilotinib (Tasigna®); Dasatinib (BMS-345825); Bosutinib (SKI-606); Ponatinib (AP24534); Bafetinib (INNO406); Danusertib (PHA-739358), AT9283 (CAS 1133385-83-7); Saracatinib (AZD0530); and N-[2-[(1S,4R)-6-[[4-(Cyclobutylamino)-5-(trifluoromethyl)-2-pyrimidinyl]amino]-1,2,3,4-tetrahydronaphthalen-1,4-imin-9-yl]-2-oxoethyl]-acetamide (PF-03814735, CAS 942487-16-3).

IGF-1R inhibitors: Linsitnib (OSI-906); [7-[trans-3-[(Azetidin-1-yl)methyl]cyclobutyl]-5-(3-benzyloxyphenyl)-7H-pyrrolo[2,3-d]pyrimidin-4-yl]amine (AEW541, CAS 475488-34-7); [5-(3-Benzyloxyphenyl)-7-[trans-3-[(pyrrolidin-1-yl)methyl]cyclobutyl]-7H-pyrrolo[2,3-d]pyrimidin-4-yl]amine (ADW742 or GSK552602A, CAS 475488-23-4); (2-[[3-Bromo-5-(1,1-dimethylethyl)-4-hydroxyphenyl]methylene]-propanedinitrile (Tyrphostin AG1024, CAS 65678-07-1); 4-[[(2S)-2-(3-Chlorophenyl)-2-hydroxyethyl]amino]-3-[7-methyl-5-(4-morpholinyl)-1H-benzimidazol-2-yl]-2(1H)-pyridinone (BMS536924, CAS 468740-43-4); 4-[2-[4-[[(2S)-2-(3-Chlorophenyl)-2-hydroxyethyl]amino]-1,2-dihydro-2-oxo-3-pyridinyl]-7-methyl-1H-benzimidazol-5-yl]-1-piperazinepropanenitrile (BMS554417, CAS 468741-42-6); (2S)-1-[4-[(5-Cyclopropyl-1H-pyrazol-3-yl)amino]pyrrolo[2,1-f][1,2,4]triazin-2-yl]-N-(6-fluoro-3-pyridinyl)-2-methyl-2-pyrrolidinecarboxamide (BMS754807, CAS 1001350-96-4); Picropodophyllotoxin (AXL1717); and Nordihydroguareacetic acid.

IGF-1R antibodies: Figitumumab (CP751871); Cixutumumab (IMC-A12); Ganitumab (AMG-479); Robatumumab (SCH-717454); Dalotuzumab (MK0646); R1507 (available from Roche); BIIB022 (available from Biogen); and MEDI-573 (available from MedImmune).

MET inhibitors: Cabozantinib (XL184, CAS 849217-68-1); Foretinib (GSK1363089, formerly XL880, CAS 849217-64-7); Tivantinib (ARQ197, CAS 1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458); Cryzotinib (Xalkori®, PF-02341066); (3Z)-5-(2,3-Dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU11271); (3Z)—N-(3-Chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide (SU11274); (3Z)—N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU11606); 6-[Difluoro[6-(1-methyl-1H-pyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N—((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin-3-yl]thio]-quinoline (SGX523, CAS 1022150-57-7); and (3Z)-5-[[(2,6-Dichlorophenyl)methyl]sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

Epidermal growth factor receptor (EGFR) inhibitors: Erlotinib hydrochloride (Tarceva®), Gefitnib (Iressa®); N-[4-[(3-Chloro-4-fluorophenyl)amino]-7-[[(3''S'')-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

EGFR antibodies: Cetuximab (Erbitux®); Panitumumab (Vectibix®); Matuzumab (EMD-72000); Trastuzumab (Herceptin®); Nimotuzumab (hR3); Zalutumumab; TheraClM h-R3; MDX0447 (CAS 339151-96-1); and ch806 (mAb-806, CAS 946414-09-1).

mTOR inhibitors: Temsirolimus (Torisel®); Ridaforolimus (formally known as deferolimus, (1R,2R,4S)-4-[(2R)-2[(1R,9S,12S,15R,16E,18R,19R,21R, 23S,24E,26E,28Z, 30S,32S,35R)-1,18-dihydroxy-19,30-dimethoxy-15,17,21, 23, 29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl]pyrido[2,3-d] pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7 (8H)-one (PF04691502, CAS 1013101-36-4); N$^2$-[1,4-dioxo-4-[[4-(4-oxo-8-phenyl-4H-1-benzopyran-2-yl) morpholinium-4-yl]methoxy]butyl]-L-arginylglycyl-L-α-aspartylL-serine-, inner salt (SF1126, CAS 936487-67-1); and N-[4-[[[3-[(3,5-dimethoxyphenyl)amino]-2-quinoxalinyl]amino]sulfonyl]phenyl]-3-methoxy-4-methyl-benzamide (XL765, also known as SAR245409); and (1r,4r)-4-(4-amino-5-(7-methoxy-1H-indol-2-Aimidazo[1,5-f][1,2,4] triazin-7-yl)cyclohexanecarboxylic acid (OSI-027).

Mitogen-activated protein kinase (MEK) inhibitors: XL-518 (also known as GDC-0973, Cas No. 1029872-29-4, available from ACC Corp.); Selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886, described in PCT Publication No. WO2003077914); 2-[(2-Chloro-4-iodophenyl)amino]-N-(cyclopropylmethoxy)-3,4-difluoro-benzamide (also known as CI-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio]methylene]-butanedinitrile (also known as U0126 and described in U.S. Pat. No. 2,779,780); N-[3, 4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3S, 4R,5Z,8S,9S,11E)-14-(Ethylamino)-8,9,16-trihydroxy-3,4-dimethyl-3,4,9,19-tetrahydro-1H-2-benzoxacyclotetradecine-1,7(8H)-dione] (also known as E6201 and described in PCT Publication No. WO2003076424); 2'-Amino-3'-methoxyflavone (also known as PD98059 available from Biaffin GmbH & Co., KG, Germany); Vemurafenib (PLX-4032, CAS 918504-65-1); (R)-3-(2,3-Dihydroxypropyl)-6-fluoro-5-(2-fluoro-4-iodophenylamino)-8-methylpyrido[2, 3-d]pyrimidine-4,7(3H,8H)-dione (TAK-733, CAS 1035555-63-5); Pimasertib (AS-703026, CAS 1204531-26-9); Trametinib dimethyl sulfoxide (GSK-1120212, CAS 1204531-25-80); 2-(2-Fluoro-4-iodophenylamino)-N-(2-hydroxyethoxy)-1,5-dimethyl-6-oxo-1,6-dihydropyridine-3-carboxamide (AZD 8330); and 3,4-Difluoro-2-[(2-fluoro-4-iodophenyl)amino]-N-(2-hydroxyethoxy)-5-[(3-oxo-[1,2] oxazinan-2-yl) methyl]benzamide (CH 4987655 or Ro 4987655).

Alkylating agents: Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Aromatase inhibitors: Exemestane (Aromasin®); Letrozole (Femara®); and Anastrozole (Arimidex®).

Topoisomerase I inhibitors: Irinotecan (Camptosar®); Topotecan hydrochloride (Hycamtin®); and 7-Ethyl-10-hydroxycampothecin (SN38).

Topoisomerase II inhibitors: Etoposide (VP-16 and Etoposide phosphate, Toposar®, VePesid® and Etopophos®); Teniposide (VM-26, Vumon®); and Tafluposide.

DNA Synthesis inhibitors: Capecitabine (Xeloda®); Gemcitabine hydrochloride (Gemzar®); Nelarabine ((2R, 3S,4R,5R)-2-(2-amino-6-methoxy-purin-9-yl)-5-(hydroxymethyl)oxolane-3,4-diol, Arranon® and Atriance®); and Sapacitabine (1-(2-cyano-2-deoxy-β-D-arabinofuranosyl)-4-(palmitoylamino)pyrimidin-2(1H)-one).

Folate Antagonists or Antifolates: Trimetrexate glucuronate (Neutrexin®); Piritrexim isethionate (BW201U); Pemetrexed (LY231514); Raltitrexed (Tomudex®); and Methotrexate (Rheumatrex®, Trexal®).

Immunomodulators: Afutuzumab (available from Roche®); Pegfilgrastim (Neulasta®); Lenalidomide (CC-5013, Revlimid®); Thalidomide (Thalomid®), Actimid (CC4047); and IRX-2 (mixture of human cytokines including interleukin 1, interleukin 2, and interferon γ, CAS 951209-71-5, available from IRX Therapeutics).

G-Protein-coupled Somatostain receptors Inhibitors: Octreotide (also known as octreotide acetate, Sandostatin® and Sandostatin LAR®); Lanreotide acetate (CAS 127984-74-1); Seglitide (MK678); Vapreotide acetate (Sanyar®); and Cyclo(D-Trp-Lys-Abu-Phe-MeAla-Tyr)(BIM23027).

Interleukin-11 and Synthetic Interleukin-11 (IL-11): Oprelvekin (Neumega®).

Erythropoietin and Synthetic erythropoietin: Erythropoietin (Epogen® and Procrit®); Darbepoetin alfa (Aranesp®); Peginesatide (Hematide®); and EPO covalently linked to polyethylene glycol (Micera®).

Histone deacetylase (HDAC) inhibitors: Voninostat (Zolinza®); Romidepsin (Istodax®); Treichostatin A (TSA); Oxamflatin; Vorinostat (Zolinza®, Suberoylanilide hydroxamic acid); Pyroxamide (syberoyl-3-ami nopyridine-amide hydroxamic acid); Trapoxin A (RF-1023A); Trapoxin B (RF-10238); Cyclo[(αS,2S)-α-amino-η-oxo-2-oxiraneoctanoyl-O-methyl-D-tyrosyl-L-isoleucyl-L-prolyl] (Cyl-1); Cyclo[(αS,2S)-α-amino-η-oxo-2-oxiraneoctanoyl-O-methyl-D-tyrosyl-L-isoleucyl-(2S)-2-piperidinecarbonyl] (Cyl-2); Cyclic[L-alanyl-D-alanyl-(2S)-η-oxo-L-α-aminooxiraneoctanoyl-D-prolyl] (HC-toxin); Cyclo[(αS,2S)-α-amino-η-oxo-2-oxiraneoctanoyl-D-phenylalanyl-L-leucyl-(2S)-2-piperidinecarbonyl] (WF-3161); Chlamydocin ((S)-Cyclic(2-methylalanyl-L-phenylalanyl-D-prolyl-η-oxo-L-α-aminooxiraneoctanoyl); Apicidin (Cyclo(8-oxo-L-2-aminodecanoyl-1-methoxy-L-tryptophyl-L-isoleucyl-D-2-piperidinecarbonyl); Romidepsin (Istodax®, FR-901228); 4-Phenylbutyrate; Spiruchostatin A; Mylproin (Valproic acid); Entinostat (MS-275, N-(2-Aminophenyl)-4-[N-(pyridine-3-yl-methoxycarbonyl)-amino-methyl]-benzamide);

and Depudecin (4,5:8,9-dianhydro-1,2,6,7,11-pentadeoxy-D-threo-D-ido-Undeca-1,6-dienitol).

Biologic response modifiers: Include therapeutics such as interferons, interleukins, colony-stimulating factors, monoclonal antibodies, vaccines (therapeutic and prophylactic), gene therapy, and nonspecific immunomodulating agents. Interferon alpha (Intron®, Roferson®-A); Interferon beta; Interferon gamma; Interleukin-2 (IL-2 or aldesleukin, Proleukin®); Filgrastim (Neupogen®); Sargramostim (Leukine®); Erythropoietin (epoetin); Interleukin-11 (oprelvekin); Imiquimod (Aldara®); Lenalidomide (Revlimid®); Rituximab (Rituxan®); Trastuzumab (Herceptin®); Bacillus calmette-guerin (theraCys® and TICE® BCG); Levamisole (Ergamisol®); and Denileukin diftitox (Ontak®).

Plant Alkaloids: Paclitaxel (Taxol and Onxal™); Paclitaxel protein-bound (Abraxane®); Vinblastine (also known as vinblastine sulfate, vincaleukoblastine and VLB, Alkaban-AQ® and Velban®); Vincristine (also known as vincristine sulfate, LCR, and VCR, Oncovin® and Vincasar Pfs®); and Vinorelbine (Navelbine®).

Taxane anti-neoplastic agents: Paclitaxel (Taxol®); Docetaxel (Taxotere®); Cabazitaxel (Jevtana®, 1-hydroxy-7β,10β-dimethoxy-9-oxo-5β,20-epoxytax-11-ene-2α,4,13α-triyl-4-acetate-2-benzoate-13-[(2R,3S)-3-{[(tert-butoxy)carbonyl]amino}-2-hydroxy-3-phenylpropanoate); and Larotaxel ((2α,3ξ,4α,5β,7α,10β,13α)-4,10-bis(acetyloxy)-13-({(2R,3S)-3-[(tert-butoxycarbonyl) amino]-2-hydroxy-3-phenylpropanoyl}oxy)-1-hydroxy-9-oxo-5,20-epoxy-7,19-cyclotax-11-en-2-yl benzoate).

Heat Shock Protein (HSP) inhibitors: Tanespimycin (17-allylamino-17-demethoxygeldanamycin, also known as KOS-953 and 17-AAG, available from SIGMA, and described in U.S. Pat. No. 4,261,989); Retaspimycin (IPI504), Ganetespib (STA-9090); [6-Chloro-9-(4-methoxy-3,5-dimethylpyridin-2-ylmethyl)-9H-purin-2-yl]amine (BIIB021 or CNF2024, CAS 848695-25-0); trans-4-[[2-(Aminocarbonyl)-5-[4,5,6,7-tetrahydro-6,6-dimethyl-4-oxo-3-(trifluoromethyl)-1H-indazol-1-yl]phenyl]amino]cyclohexyl glycine ester (SNX5422 or PF04929113, CAS 908115-27-5); and 17-Dimethylaminoethylamino-17-demethoxygeldanamycin (17-DMAG).

Thrombopoietin (TpoR) agonists: Eltrombopag (SB497115, Promacta® and Revolade®); and Romiplostim (Nplate®).

Demethylating agents: 5-Azacitidine (Vidaza®); and Decitabine (Dacogen®).

Cytokines: Interleukin-2 (also known as aldesleukin and IL-2, Proleukin®); Interleukin-11 (also known as oprevelkin, Neumega®); and Alpha interferon alfa (also known as IFN-alpha, Intron® A, and Roferon-A®).

17α-hydroxylase/C17,20 lyase (CYP17A1) inhibitors: Abiraterone acetate (Zyitga®).

Miscellaneous cytotoxic agents: Arsenic trioxide (Trisenox®); Asparaginase (also known as L-asparaginase, Erwinia L-asparaginase, Elspar® and Kidrolase®); and Asparaginase Erwinia Chrysanthemi (Erwinaze®).

C-C Chemokine receptor 4 (CCR4) Antibody: Mogamulizumab (Potelligent®)

CD20 antibodies: Rituximab (Riuxan® and MabThera®); and Tositumomab (Bexxar®); and Ofatumumab (Arzerra®).

CD20 Antibody Drug Conjugates: Ibritumomab tiuxetan (Zevalin®); and Tositumomab, CD22 Antibody Drug Conjugates: Inotuzumab ozogamicin (also referred to as CMC-544 and WAY-207294, available from Hangzhou Sage Chemical Co., Ltd.)

CD30 mAb-cytotoxin Conjugates: Brentuximab vedotin (Adcetrix®);

CD33 Antibody Drug Conjugates: Gemtuzumab ozogamicin (Mylotarg®),

CD40 antibodies: Dacetuzumab (also known as SGN-40 or huS2C6, available from Seattle Genetics, Inc), CD52 antibodies: Alemtuzumab (Campath®), Anti-CS1 antibodies: Elotuzumab (HuLuc63, CAS No. 915296-00-3)

CTLA-4 inhibitor antibodies: Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

TPH inhibitors: telotristat

PARP (poly ADP ribose polymerase) inhibitors: olaparib (Lynparza), rucaparib (Rubraca), Niraparib (Zeluja), Talazoparib, Veliparib.

PD-1 Inhibitors: Spartalizumab (PDR001, Novartis), Nivolumab (Bristol-Myers Squibb), Pembrolizumab (Merck & Co), Pidilizumab (CureTech), MEDI0680 (Medimmune), REGN2810 (Regeneron), TSR-042 (Tesaro), PF-06801591 (Pfizer), BGB-A317 (Beigene), BGB-108 (Beigene), INCSHR1210 (Incyte), or AMP-224 (Amplimmune).

PD-L1 inhibitors: Durvalumab, Atezolizumab, Avelumab

In particular, the present invention provides the combination or combination therapy of the complex formed by the radionuclide $^{177}$Lu (Lutetium-177), and a somatostatin receptor binding peptide linked to the chelating agent as defined herein, or the combination or combination therapy of the pharmaceutical aqueous solution as defined herein, together with one of more therapeutic agents selected from the group consisting of octreotide, lanreotide, vaproreotide, pasireotide, satoreotide, everolimus, temozolomide, telotristat, sunitinib, sulfatinib, ribociclib, entinostat, and pazopanib. In particular embodiments, those combinations are for use in the treatment of NET tumors, e.g. GEP-NET, pulmonary NET, pNET, lung NET, Carcinoid syndrome, SCLC. In particular embodiments, the invention provides a method of treating a patient with NET tumors, e.g. GEP-NET, pulmonary NET, pNET, lung NET, Carcinoid syndrome, SCLC, by administering a therapeutically effective amount of the components of those combinations.

In particular embodiments, the present invention provides the combination or combination therapy of the complex formed by the radionuclide $^{177}$Lu (Lutetium-177), and a somatostatin receptor binding peptide linked to the chelating agent as defined herein, or the combination or combination therapy of the pharmaceutical aqueous solution as defined herein, together with one of more immuno-oncology therapeutic agents selected from the group consisting of PD-1, PD-L1 and CTLA-4 inhibitors, in particular the I-O therapeutic agents selected from Spartalizumab, Nivolumab, Pembrolizumab, Pidilizumab, Durvalumab, Atezolizumab, Avelumab, Ipilimumab, and Tremelimumab. In particular embodiments, those combinations are for use in the treatment of NET tumors, e.g. GEP-NET, pulmonary NET, pNET, lung NET, Carcinoid syndrome, SCLC. In particular embodiments, the invention provides a method of treating a patient with NET tumors, e.g. GEP-NET, pulmonary NET, pNET, lung NET, Carcinoid syndrome, SCLC, by administering a therapeutically effective amount of the components of those combinations.

DEFINITIONS

In the following, terms as used herein are defined in their meaning.

The use of the articles "a", "an", and "the" in both the description and claims are to be construed to cover both the singular and the plural, unless otherwise indicated herein or clearly contradicted by context. The terms "comprising", "having", "being of" as in e.g., a complex "of a radionuclide and a cell receptor binding organic moiety linked to a chelating agent", "including", and "containing" are to be construed as open terms (i.e., meaning "including but not limited to") unless otherwise noted. Additionally, whenever "comprising" or another open-ended term is used in an embodiment, it is to be understood that the same embodiment can be more narrowly claimed using the intermediate term "consisting essentially of" or the closed term "consisting of".

The term "about" or "ca." has herein the meaning that the following value may vary for ±20%, preferably ±10%, more preferably ±5%, even more preferably ±2%, even more preferably ±1%.

Unless otherwise defined, "%" has herein the meaning of weight percent (wt %), also referred to as weight by weight percent (w/w %).

"total concentration": sum of one or more individual concentrations.

"aqueous solution": a solution of one or more solute in water.

"complex formed by
  (ai) a radionuclide, and
  (aiii) a cell receptor binding organic moiety linked to a chelating agent":

The radionuclide metal ion is forming a non-covalent bond with the functional groups of the chelating agent, e.g. amines or carboxylic acids. The chelating agent has at least two such complexing functional groups to be able to form a chelate complex.

The chelating agent in the context of the present invention may be

DOTA: 1,4,7,10-Tetraazacyclododecane-1,4,7,10-tetraacetic acid,
DTPA: Diethylentriaminepentaacetic acid,
NTA: Nitrilotriacetic acid,
EDTA: Ethylenediaminetetraacetic acid,
DO3A: 1,4,7,10-Tetraazacyclododecane-1,4,7-triacetic acid,
NOTA: 1,4,7-Triazacyclononane-1,4,7-triacetic acid,
Trizoxetan,
Tetraxetan
or mixtures thereof, preferably is DOTA.

"cell receptor binding moiety": a chemical molecule which binds with at least part of its molecule to a receptor molecule at the surface of a cell. A cell receptor binding moiety, for which the present invention is in particular suitable, is a somatostatin receptor binding peptide, preferably said somatostatin receptor binding peptide is selected from octreotide, octreotate, lanreotide, vapreotide, pasireotide, ilatreotide, pentetreotide, depreotide, satoreotide, veldoreotide, preferably selected from octreotide and octreotate.

"linked": the cell receptor binding organic moiety is either directly linked to the chelating agent or connected via a linker molecule, preferably it is directly linked. The linking bond(s) is (are) either covalent or non-covalent bond(s) between the cell receptor binding organic moiety (and the linker) and the chelating agent, preferably the bond(s) is (are) covalent.

"Stabilizer against radiolytic degradation": stabilizing agent which protects organic molecules against radiolytic degradation, e.g. when a gamma ray emitted from the radionuclide is cleaving a bond between the atoms of an organic molecules and radicals are formed, those radicals are then scavenged by the stabilizer which avoids the radicals undergoing any other chemical reactions which might lead to undesired, potentially ineffective or even toxic molecules. Therefore, those stabilizers are also referred to as "free radical scavengers" or in short "radical scavengers". Other alternative terms for those stabilizers are "radiation stability enhancers", "radiolytic stabilizers", or simply "quenchers".

"stabilizer(s) is (are) present in the solution during the complex formation of components (ai) and (aiii)": first stabilizer present and optionally also second stabilizer present, i.e. either first stabilizer alone or in combination with second stabilizer present "present during the complex formation": stabilizer(s) are in either the radionuclide solution or in the chelating agent containing solution before those two solutions are added and potentially elevated temperatures are applied to facilitate the complex formation. Preferably the stabilizer(s) are in the chelating agent containing solution.

"only the first stabilizer is present during the complex formation of components (ai) and (aiii)": the first stabilizer is present, the second is not present. In other words only one stabilizer is present.

"second stabilizer is added after the complex formation of components (ai) and (aiii)": Regardless of whether the second stabilizers may have been present already during the complex formation or not, the second stabilizer is added after the complex forming reaction is completed, e.g. after the reacting solution which might have been heated up to an elevated temperature is again cooled down to ambient temperature.

The cell receptor binding moiety and the chelating agent may form together the following molecules:

DOTA-OC: [DOTA⁰,D-Phe¹]octreotide,
DOTA-TOC: [DOTA⁰,D-Phe¹,Tyr³]octreotide, edotreotide (INN),
represented by the following formulas:

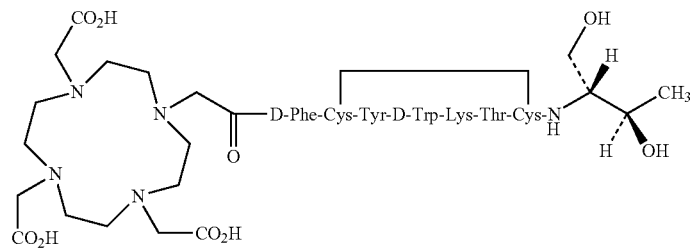

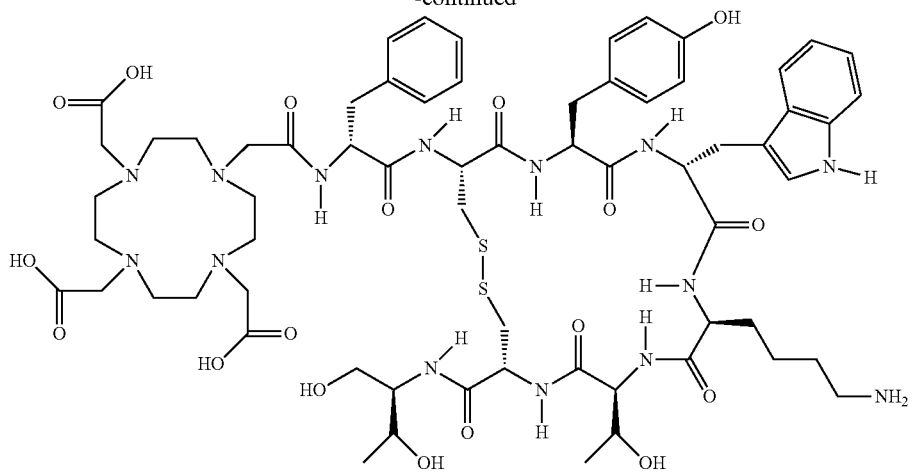

DOTA-NOC: [DOTA⁰,D-Phe¹,1-Nal³]octreotide,
DOTA-TATE: [DOTA⁰,D-Phe¹,Tyr³]octreotate, DOTA-Tyr³-Octreotate, DOTA-d-Phe-Cys-Tyr-d-Trp-Lys-Thr-Cys-Thr (cyclo 2,7), oxodotreotide (INN), represented by the following formula:

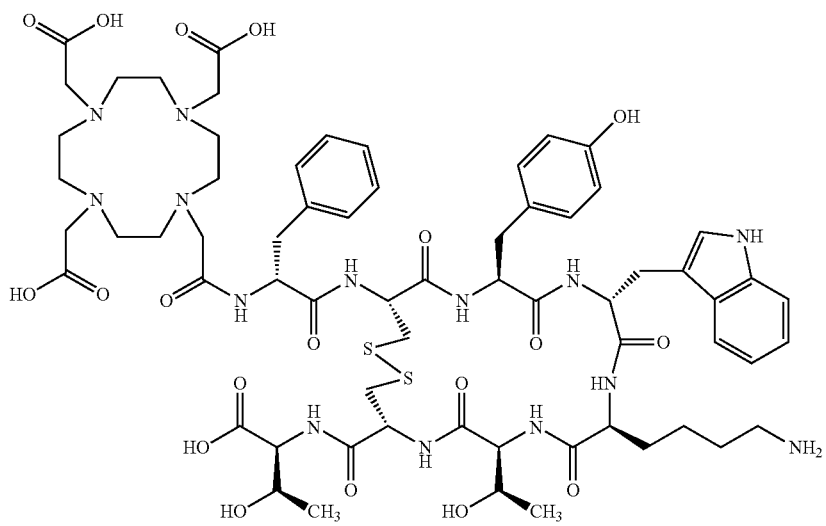 [SMILES: C[C@@H](O)[C@H](NC(=O)[C@@H]1CSSC[C@H](NC(=O)[C@@H](Cc2ccccc2)NC(=O)CN2CCN(CC(=O)O)CCN(CC(=O)O)CCN(CC(=O)O)CC2)C(=O)N[C@@H](Cc2ccc(O)cc2)C(=O)N[C@H](Cc2c[nH]c3ccccc23)C(=O)N[C@@H](CCCCN)C(=O)N[C@@H]([C@@H](C)O)C(=O)N1)C(=O)O]

DOTA-LAN: [DOTA⁰,D-β-Nal¹]lanreotide,
DOTA-VAP: [DOTA⁰,D-Phe¹,Tyr³]vapreotide.

Satoreotide Trizoxetan

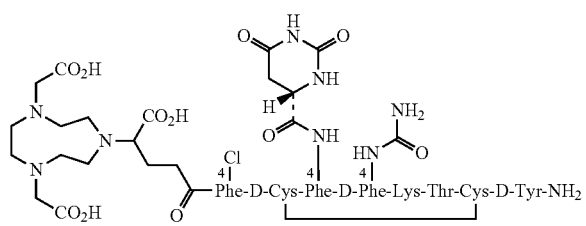

Satoreotide Tetraxetan

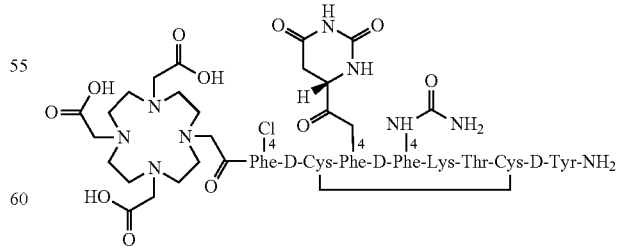

The preferred "cell receptor binding moiety linked to the chelating agent" molecules for the present invention are DOTA-TOC, DOTA-TATE, and Satoreotide tetraxetan, more preferably the molecule is DOTA-TATE.

For the present invention, the preferred complex formed by (or the preferred complex of) the radionuclide and the cell receptor binding moiety linked to the chelating agent according to the present invention is $^{177}$Lu-DOTA-TATE, which is also referred to as Lutetium (177Lu) oxodotreotide (INN), i.e. hydrogen [N-{[4,7,10-tris(carboxylato-κO-methyl)-1,4,7,10-tetraazacyclododecan-1-yl-κ$N^1$, $N^4$,$N^7$,$N^{10}$]acetyl-κO}-D-phenylalanyl-L-cysteinyl-tyrosyl-D-tryptophyl-L-lysyl-L-threonyl-L-cysteinyl-L-threoninato cyclic (2→7)-disulfide(4-)](177Lu)lutetate (1-)
and is represented by the following formulas:

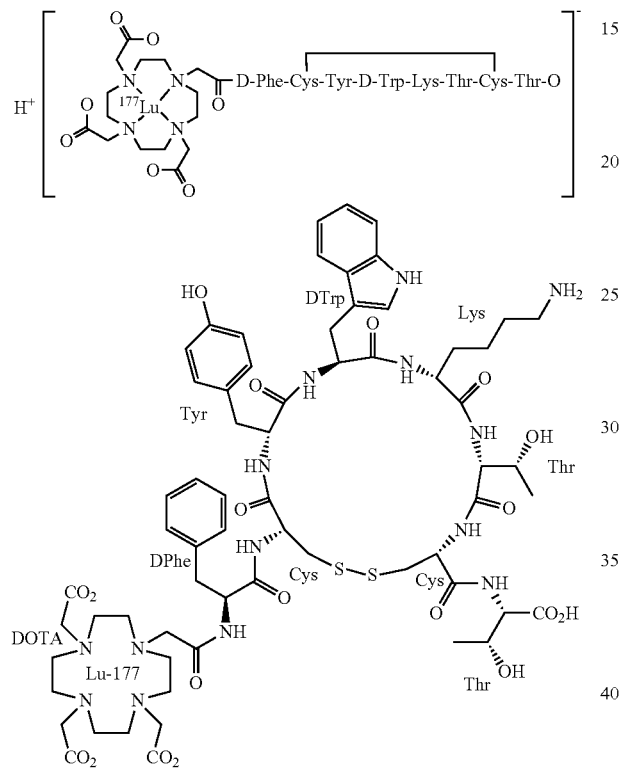

"Buffer for a pH from 4.5 to 6.0": may be an acetate buffer, citrate buffer (e.g. citrate+HCl or citric acid+Disodium hydrogenphosphate) or phosphate buffer (e.g. Sodium dihydrogenphosphate+Disodium hydrogenphosphate), preferably said buffer is an acetate buffer, preferably said acetate buffer is composed of acetic acid and sodium acetate.

"Sequestering agent", a chelating agent suitable to complex the radionuclide metal ions, preferably DTPA: Diethylentriaminepentaacetic acid.

"for commercial use": the drug product, e.g. a pharmaceutical aqueous solution, is able to obtain (preferably has obtained) marketing authorization by health authorities, e.g. US-FDA or EMA, by complying with all drug product quality and stability requirements as demanded by such health authorities, is able to be manufactured (preferably is manufactured) from or at a pharmaceutical production site at commercial scale followed by a quality control testing procedure, and is able to be supplied (preferably is supplied) to remotely located end users, e.g. hospitals or patients.

"Combination": refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent.

EXAMPLES

Hereinafter, the present invention is described in more details and specifically with reference to the examples, which however are not intended to limit the present invention.

Materials:

The $^{177}$LuCl$_3$ may be obtained from commercial sources, e.g. I.D.B. Holland BV. The DOTA$^0$-Tyr$^3$-Octreotate may be obtained from commercial sources, e.g. by piCHEM Forschungs- und Entwicklungs GmbH, Austria. All other components of the drug product are commercially available from various sources.

Example 1

Composition of Drug Product

The Drug Product ($^{177}$Lu-DOTM-Tyr$^3$-Octreotate 370 MBq/mL solution for infusion) is designed as a sterile ready-to-use solution for infusion containing $^{177}$Lu-DOTA$^0$-Tyr$^3$-Octreotate as Drug Substance with a volumetric activity of 370 MBq/mL at reference date and time (calibration time (tc)). Calibration time (tc) corresponds to the End of Production (EOP=t0) which is the time of measurement of the activity of the first QC vial. The shelf-life of Drug Product is defined as 72 hours after calibration time. Drug Product is a single dose vial, containing suitable amount of solution that allows delivery of 7.4 GBq of radioactivity at injection time.

Manufacturing site prepares single doses calibrated within the range of 7.4 GBq±10% (200 mCi) after the end of production. Certificates of analysis reports both the exact activity provided and the time when this activity is reached. This value is declared as "Injection time: {DD MM YYYY} {hh:mm} UTC". Considering the variable injection time and constant decay of the radionuclide, the filling volume needed for an activity of 7.4 GBq at injection time is calculated and can range from 20.5 and 25.0 mL.

Composition of Drug Product per mL

| Property/Component | Quantity (Unit/mL) | Function |
|---|---|---|
| $^{177}$Lu-DOTA$^0$-Tyr$^3$-Octreotate (volumetric activity) | 370 MBq/mL at $t_c$ (EOP) | Drug Substance |
| X-DOTA$^0$-Tyr$^3$-Octreotate | 10 µg/mL | Total peptide content |
| Specific Activity (GBq/Total peptide) | ≥53 GBq/µmol at EOP | NA |
| Excipients | | |
| Acetic acid | 0.48 mg/mL | pH adjuster |
| Sodium acetate | 0.66 mg/mL | pH adjuster |
| Gentisic acid | 0.63 mg/mL | RSE |
| Ascorbic acid | 2.80 mg/mL | RSE |
| DTPA | 0.05 mg/mL | Sequestering agent |
| Sodium chloride (NaCl) | 6.85 mg/mL | Isotonizing agent |
| Sodium hydroxide (NaOH) | 0.64 mg/mL | pH adjuster |
| Water for injection | Ad 1 mL | Solvent |

EOP: End of Production = $t_0$ = activity measurement of the first vial = calibration time $t_c$
RSE: Radiation Stability Enhancer Example 2

Manufacturing of Drug Product

For a 74 GBq batch size (2 Ci batch size) a $^{177}$LuCl$_3$ solution, about 74 GBq in HCl, is mixed together with a DOTA-Tyr$^3$-Octreotate (about 2 mg) solution, and a Reaction Buffer solution, containing an antioxidant agent (and stabilizer against radiolytic regradation) (i.e. Gentisic acid, about 157 mg) and a buffer system (i.e. Acetate buffer system), resulting in a total of about 5.5 mL solution, which is used for radiolabelling that occurs at a temperature of about 90 to about 98° C. within less than 15 minutes.

The synthesis is carried out using a single use disposable kit cassette installed on the front of the synthesis module which contains the fluid pathway (tubing), reactor vial and sealed reagent vials.

The obtained mother solution is diluted with a solution containing a chelating agent (i.e. DTPA), an antioxidant agent (i.e. Ascorbic acid) sodium hydroxide, and sodium chloride and, then sterile filtered through 0.2 µm to give the ready-to-use solution as described in Example 1 with a pH of 4.5-6.0, in particular 5.2-5.3. Finally, the solution is dispensed in volumes of from 20.5 to 25.0 mL into sterile vials. The stoppered vials are enclosed within lead containers for protective shielding.

Manufacturing Process can also be implemented for batch sizes higher than 74 GBq. In this case the amount of the raw materials (Lutetium, peptide and Reaction Buffer) are multiplied to guarantee the same raw materials ratio.

Example 3

Stability Study Results After Storage at Various Temperature Conditions

The following table provides the stability test data for a batch produced at 74 GBq batch size according to the process described in Example 2.

| Time points | | t(0) | t(0 + 24 h) | t(0 + 48 h) | t(0 + 72 h) |
|---|---|---|---|---|---|
| Stability at 5 ± 2° C. | | CQ1 | | | 11 mL 21.8 mL |
| pH | | 5.3 | n.d. | n.d. | 5.3 5.3 |
| Chemical purity (RP-UV-HPLC) | Peptide purity (%) | 100.0 | n.d. | n.d. | 100.0 100.0 |
| Radiochemical purity (RP-γβ-HPLC) | $^{177}$Lu-DOTA$^0$-Tyr$^3$-octreotate (%) | 98.37 | n.d. | n.d. | 96.09 96.40 |
| Stability at 25 ± 2° C. | | CQ1 | 5 mL | 5 mL | 5 mL 24.7 mL |
| pH | | 5.3 | 5.3 | 5.2 | 5.2 5.3 |
| Chemical purity (RP-UV-HPLC) | Peptide purity (%) | 100.0 | 100.0 | 100.0 | 100.0 |
| Radiochemical purity (RP-γβ-HPLC) | $^{177}$Lu-DOTA$^0$-Tyr$^3$-octreotate (%) | 98.28 | 96.99 | 96.29 | 95.02 95.62 |
| Stability at 32 ± 2° C. | | CQ1 | 5.6 mL 22.2 mL | 5.6 mL 22.2 mL | |
| pH | | 5.3 | n.d. | 5.3 5.3 | n.d. |
| Chemical purity (RP-UV-HPLC) | Peptide purity (%) | 100.0 | 100.0 100.0 | 100.0 100.0 | n.d. |
| Radiochemical purity (RP-γβ-HPLC) | $^{177}$Lu-DOTA$^0$-Tyr$^3$-octreotate (%) | 98.37 | 96.03 96.51 | 94.45 95.45 | n.d. |

-continued

| Time points | | t(0) | t(0 + 24 h) | t(0 + 48 h) | t(0 + 72 h) |
|---|---|---|---|---|---|
| Stability at 32 ± 2° C. per 12 h and at 25 ± 2° C. per 60 h | | CQ1 | | | 11 mL |
| Chemical purity (RP-UV-HPLC) | Peptide purity (%) | 100.0 | n.d. | n.d. | 100.0 |
| Radiochemical purity (RP-γβ-HPLC) | $^{177}$Lu-DOTA$^0$-Tyr$^3$-octreotate (%) | 98.28 | n.d. | n.d. | 95.01 |

"n.d." = not determined;
"LOD" = limit of detection

Very similar good stability results were obtained for batches produced at 148 GBq batch size.

The invention claimed is:

1. A process for manufacturing a pharmaceutical aqueous solution, comprising:
   providing a solution comprising a complex of the radionuclide $^{177}$Lu (Lutetium-177) and a somatostatin receptor binding peptide linked to the chelating agent DOTA; a first stabilizer against radiolytic degradation, and optionally a second stabilizer against radiolytic degradation different from the first stabilizer; and
   diluting the solution comprising the complex with an aqueous dilution solution comprising at least one stabilizer against radiolytic degradation to obtain the pharmaceutical aqueous solution;
   wherein if the solution comprising the complex comprises only the first stabilizer as an stabilizer against radiolytic degradation and not the second stabilizer, then the aqueous dilution solution comprises at least one stabilizer against radiolytic degradation that is different from the first stabilizer, and in the obtained pharmaceutical aqueous solution, the radionuclide $^{177}$Lu is present in a concentration that it provides a volumetric radioactivity of from 250 to 500 MBq/mL and the stabilizers are present in a total concentration of from 1.0 to 5.0 mg/mL, and ethanol is present in a concentration of less than 1%.

2. The process according to claim 1, comprising:
   (1) forming a complex of the radionuclide $^{177}$Lu and a somatostatin receptor binding peptide linked to the chelating agent DOTA by
      (1.1) providing an aqueous solution comprising the radionuclide;
      (1.2) providing an aqueous solution comprising the a somatostatin receptor binding peptide linked to the chelating agent, and a first stabilizer against radiolytic degradation and optionally a second stabilizer against radiolytic degradation different from the first stabilizer; and
      (1.3) mixing the solutions provided in steps (1.1) and (1.2) and heating the resulting mixture to form a solution comprising the complex;
   (2) diluting the solution comprising the complex obtained by step (1) by
      (2.1) providing an aqueous dilution solution comprising at least one stabilizer against radiolytic degradation; and
      (2.2.) mixing the solution comprising the complex obtained by step (1) with the dilution solution provided in step (2.1) to obtain the pharmaceutical aqueous solution;
   wherein if the solution in step (1.2) comprises only one stabilizer that is the first stabilizer, then the solution in step (2.1) comprise at least one stabilizer that is different from the first stabilizer.

3. The process according to claim 2, wherein the solution in step (1.2) comprises the first stabilizer and the solution provided in step (2.1) comprises at least one stabilizer.

4. The process according to claim 2, wherein at least gentisic acid or a salt thereof is provided in step (1.2) and the solution provided in step (2.1) comprises at least ascorbic acid or a salt thereof.

5. The process according to claim 2, wherein only one stabilizer which is gentisic acid or a salt thereof is provided in step (1.2) and the solution provided in step (2.1) comprises only one stabilizer which is ascorbic acid or a salt thereof.

6. The process according to claim 2, wherein the stabilizer/stabilizers provided in step (1.2) is/are present during the complex formation in step (1.3) in a total concentration of from 15 to 50 mg/mL.

7. The process according to claim 6, wherein the stabilizer/stabilizers provided in step (1.2) is/are present during the complex formation in step (1.3) in a total concentration of from 20 to 40 mg/mL.

8. The process according to claim 7, wherein the only one stabilizer provided in step (1.2) is gentisic acid and the stabilizer is present during the complex formation in step (1.3) in a concentration of from 20 to 40 mg/mL.

9. The process according to claim 8, wherein the only one stabilizer provided in step (1.2) is gentisic acid and the stabilizer is present during the complex formation in step (1.3) in a concentration of from 25 to 35 mg/mL.

10. The process according to claim 9, wherein the solution provided in step (1.2) further comprises a buffer.

11. The process according to claim 10, wherein the buffer is an acetate buffer.

12. The process according to claim 2, wherein in step (1.3) the resulting mixture is heated to a temperature of from 70 to 99° C., for from 2 to 59 min.

13. The process according to claim 12, wherein in step (1.3) the resulting mixture is heated to a temperature of from 90 to 98° C. for from 5 to 15 min.

14. The process according to claim 2, wherein the solution provided in step (2.1) further comprises diethylentriaminepentaacetic acid (DTPA) or a salt thereof.

15. The process according to claim 2, further comprising the process steps:
   (3) filtering the solution obtained by step (2) through 0.2 μm; and
   (4) dispensing the filtered solution obtained by step (3) into dose unit containers in a volume required to deliver the radioactive dose of 7.4 GBq±10%.

16. The process according to claim 2, wherein the solution of step (1.1) comprises LuCl$_3$ and HCl.

17. The process according to claim 2, wherein the solution of step (1.2) comprises $^{177}$Lu-DOTA-TATE or $^{177}$Lu-DOTA-TOC, gentisic acid, acetic acid, and sodium acetate.

18. The process according to claim 2, wherein the solution of step (2.1) comprises DTPA and ascorbic acid.

19. The process according to claim 15, wherein the dose unit containers in step (4) are stoppered vials, enclosed within a lead container.

20. The pharmaceutical aqueous solution obtained by the process of claim 1.

21. The pharmaceutical aqueous solution according to claim 20, which is free of ethanol.

22. The pharmaceutical aqueous solution according to claim 20, wherein the stabilizers in the obtained pharmaceutical aqueous solution consists essentially of gentisic acid or a salt thereof and ascorbic acid or a salt thereof.

23. The pharmaceutical aqueous solution according to claim 22, wherein the stabilizers are present in a total concentration of from about 2.7 to about 4.1 mg/mL.

24. The pharmaceutical aqueous solution according to claim 22, for which the radiochemical purity (determined by HPLC) is maintained at ≥95% for at least 72 h when stored at 25° C.

\* \* \* \* \*